US009845349B2

(12) United States Patent
Goldstein et al.

(10) Patent No.: US 9,845,349 B2
(45) Date of Patent: Dec. 19, 2017

(54) REGULATING BACILLUS ANTHRACIS LETHAL FACTOR ACTIVITY VIA AN ACTIVATING EPITOPE REGION

(71) Applicant: The United States of America, as represented by the Secretary, Department of Health and Human Services, Rockville, MD (US)

(72) Inventors: Jason Marc Goldstein, Decatur, GA (US); Conrad P. Quinn, Lilburn, GA (US); Dennis A. Bagarozzi, Jr., Lilburn, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/694,627

(22) Filed: Apr. 23, 2015

(65) Prior Publication Data

US 2016/0272698 A1    Sep. 22, 2016

Related U.S. Application Data

(63) Continuation of application No. 14/427,329, filed as application No. PCT/US2013/059179 on Sep. 11, 2013.

(60) Provisional application No. 61/699,738, filed on Sep. 11, 2012.

(51) Int. Cl.
C07K 16/12    (2006.01)
C07K 7/00    (2006.01)

(52) U.S. Cl.
CPC ............ *C07K 16/1278* (2013.01); *C07K 7/00* (2013.01); *C07K 2317/34* (2013.01); *C07K 2317/75* (2013.01)

(58) Field of Classification Search
CPC ............ C07K 16/1278; C07K 2317/24; C07K 2317/34; C07K 2317/51; C07K 2317/515; C07K 2317/75; C07K 14/32; C07K 7/06; C07K 7/08; A61K 39/07; C12N 9/54; C12Y 304/24083

See application file for complete search history.

(56) References Cited

U.S. PATENT DOCUMENTS

| | | | |
|---|---|---|---|
| 7,794,732 B2 | 9/2010 | James et al. | |
| 2002/0120106 A1 | 8/2002 | Bogoch et al. | |
| 2010/0172926 A1 | 7/2010 | James et al. | |
| 2011/0021748 A1 | 1/2011 | Cunningham et al. | |
| 2011/0110954 A1 | 5/2011 | James et al. | |
| 2013/0332133 A1* | 12/2013 | Horn ..................... | C12N 9/00 703/11 |

FOREIGN PATENT DOCUMENTS

WO    2011057011 A2    5/2011

OTHER PUBLICATIONS

Campbell AM. In: Monoclonal Antibody Technology. Elsevier Science Publishers, The Netherlands, Chapter 1, pp. 1-32, 1984.*
Albrecht, M.T. et al., "Human Monoclonal Antibodies against Anthrax Lethal Factor and Protective Antigen Act Independently To Protect against Bacillus anthracis Infection and Enhance Endogenous Immunity to Anthrax," Infection and Immunity, vol. 75, No. 11, p. 5425-5433 (Nov. 2007).
Boyer, A.E. et al., "Detection and Quantification of Anthrax Lethal Factor in Serum by Mass Spectrometry," Anal. Chem. 2007, 79, p. 8463-8470.
Boyer, A.E., "Quantitative Mass Spectrometry for Bacterial Protein Toxins—A Sensitive, Specific, High-Throughput Tool for Detection and Diagnosis," Molecules 2011, 16, p. 2391-2413.
Dalkas, G.A. et al., "Insights into the anthrax lethal factor-substrate interaction and selectivity using docking and molecular dynamics simulations," Protein Science 2009, vol. 18:1774-1785.
International Search Report and Written Opinion for co-pending PCT application Serial No. PCT/US13/59179, dated Aug. 13, 2014
Da Mota, F. et al., "Assessment of the diversity of *Paenibacillus* species in environmental samples by a novel rpoB-based PCR-DGGE method," FEMS Microbiology Ecology 53 (2005), p. 317-328.
Ingram, R.J. et al., "Natural Exposure to Cutaneous Anthrax Gives Long-Lasting T Cell Immunity Encompassing Infection-Specific Epitopes," J Immunol 2010; 184:3814-3821.
Jiao, G. et al., "Antidotes to anthrax lethal factor intoxication. Part 3: Evaluation of core structures and further modifications to the C2-side chain," Bioorg Med Chem Lett. Mar. 15, 2012; 22(6): 2242-2246.
Pannifer, A.D. et al., "Crystal structure of the anthrax lethal factor," Nature, vol. 414, Nov. 8, 2001, pp. 229-233.
Nguyen, M.L. et al., "Sequential B-Cell Epitopes of Bacillus anthracis Lethal Factor Bind Lethal Toxin-Neutralizing Antibodies," Infection and Immunity, Jan. 2009, vol. 77, No. 1, p. 162-169.
Quinn, C.P. et al., "Functional Mapping of Anthrax Toxin Lethal Factor by In-frame Insertion Mutagenesis," The Journal of Biological Chemistry, vol. 266, No. 30, Oct. 25, 1991, pp. 20124-20130.
Rosovitz, M.J. et al., "Alanine-scanning Mutations in Domain 4 of Anthrax Toxin Protective Antigen Reveal Residues Important for Binding to the Cellular Receptor and to a Neutralizing Monoclonal Antibody," The Journal of Biological Chemistry, vol. 278, No. 33, Aug. 15, 2003, pp. 30936-30944.
Database UniProt (Online) Aug. 1, 1990, "RecName: Full=Defensin-1; AltName: Full=Royalisin; Flags: Precursor;", XP002755467, retrieved from EBI accession No. UNIPROT: P17722 Database accession No. P17722 * sequence *.
Database Registry (Online) Chemical Abstracts Service, Columbus, Ohio, US; Mar. 5, 2012, "L-Aspartic acid, glycylglycyl-L-seryl-L-phenylalanyl-L-arginyl-", XP002755546, Database accession No. 1359845-60-5 * sequence *.
Database Registry (Online) Chemical Abstracts Service, Columbus, Ohio, US; May 23, 2012, "L-Serine, L-leucyl-L-alanyl-L-seryl-L-histidyl-L-arginyl-L-.alpha.-glutamy1-", XP992755547, Database accession No. 1374338-09-6 * sequence.
Database Registry (Online) Chemical Abstracts Service, Columbus, Ohio, US; Dec. 30, 2011, "L-Aspartic acid, L-threonyl-L-histidyl-L-lysyl_L-.alpha.-glutamyl-L-isoleucyl-L-valyl-", XP002755548, Database accession No. 1352120-80-9 * sequence *.

(Continued)

*Primary Examiner* — S. Devi
(74) *Attorney, Agent, or Firm* — Sheridan Ross P.C.

(57) ABSTRACT

Provided are antibodies capable of binding to a particular epitope or specifically binding to LF or LTx and enhancing the activity of the LF or LTx relative to the LF or LTx absent the antibody binding.

5 Claims, 11 Drawing Sheets

(56) References Cited

OTHER PUBLICATIONS

Database Registry (Online) Chemical Abstracts Service, Columbus, Ohio, US; May 7, 2009, "L-Alanine, L-alanyl-L-alanyl-L-seryl-L-alanyl-L-arginyl-L-.alpha.-aspartylglyc yl-", XP002755549, Database accession No. 1143554-38-4 * sequence.

Database Registry (Online) Chemical Abstracts Service, Columbus, Ohio, US; Mar. 24, 2010, "Glycine, L-threonyl-L-alanyl-L-lysyl-L-.alpha.-aspartylglycyl-L-alanyl-L-prolyl-", XP002755550, Database accession No. 1213762-52-7 * sequence *.

Database Registry (Online) Chemical Abstracts Service, Columbus, Ohio, US; Apr. 2, 2004, "Transcription-associated protein (Glycine max clone PAT_MRT3847_25922c.1.pep fragment)", XP002755551, Database accession No. 670379-92-7 * sequence *.

* cited by examiner

```
                 10        20        30        40        50        60
                  |         |         |         |         |         |
SEQ ID NO: 43   EVQLQVSGAELVRPGASVRLSCKASGYTFTSYYIYWVKQRPGQGLEWIGDI
SEQ ID NO: 44   -VQLQESGAELVRPGASVRLSCKASGYTFTSYYIYWVKQRPGQGLEWIGDI
SEQ ID NO: 42   EVQLHESGAELVRPGASVRLSCKASGYTFTSYYIYWVKQRPGQGLEWIGDI
                  **:**********************************************

SEQ ID NO: 63   EVQLQESGAELVRPGASVRLSCKASGYTFTSYYIYWVKQRPGQGLEWIGDI 70        80        90       100       110       120
                  |         |         |         |         |         |
                NPSDGDTDFNEKFKSKATLTVDKSSSTAYMETQLSSLTSEDSAVYYCTRSRGGFAYWGQG
                NPSDGDTDFNEKFKSKATLTVDKSSSTAYMETQLSSLTSEDSAVYYCTRSRGGFAYWGQG
                NPSDGDTDFNEKFKSKATLTVDKSSSTAYMETQLSSLTSEDSAVYYCTRSRGGFAYWGQG
                ************************************************************

NPSDGDTDFNEKFKSKATLTVDKSSSTAYMETQLSSLTSEDSAVYYCTRSRGGFAYWGQG 130       140       150       160       170
                  |         |         |         |         |
                TLVTVSAAKTTPPSVYPLAPGSAAQTNSMETVTLGCLVKGYFPEPVTVTWNSGS-
                TLVTVSAAKTTPPSVYPLAPGSAAQTNSMETVTLGCLVKGYFPEPVTVTWNSGS-
                TLVTVSAAKTTPPSVYPLAPGSAAQTNSMETVTLGCLVKGYFPEPVTVTWNSGSL
                ******************************************************

TLVTVSAAKTTPPSVYPLAPGSAAQTNSMETVTLGCLVKGYFPEPVTVTWNSGSL
```

FIG. 5

SEQ ID NO: 45 --------ISSRSSQSIVHSNGNTYLEWYLQKPAQSPKLLIFKVSNRFSGVPDRFSRSGSG
SEQ ID NO: 46 SHGDQASISSRSSQSIVHSNGNTYLEWYLQKPAQSPKLLIFKVSNRFSGVPDRFSRSGSG
SEQ ID NO: 47 --------ISSRSSQSAVHSNGNTYLEWYRRNPAQSPKLLIIKVSNRFSGVPDRFSHSGSG
               ******  ******** :;*****;***********:**

TDFTLKISRVEAEDLGIYYCFQGSHVPWTF------
TDFTLKISRVEAEDLGIYYCFQGSHVPWTFGGGTKL
TDFTLKISRVEAEDLGIYYCFQGSHV----------
*************************

REGULATING BACILLUS ANTHRACIS LETHAL FACTOR ACTIVITY VIA AN ACTIVATING EPITOPE REGION

CROSS REFERENCE TO RELATED APPLICATIONS

This application is a continuation-in-part of pending U.S. application Ser. No. 14/427,329, filed Mar. 11, 2015, which is the U.S. national phase of PCT Application No: PCT/US2013/059179, filed Sep. 11, 2013, now expired, which depends from and claims priority to U.S. Provisional Application No. 61/699,738 filed Sep. 11, 2012, the entire contents of each of which are incorporated herein by reference.

GOVERNMENT INTEREST

The invention described herein may be manufactured, used, and licensed by or for the United States Government.

REFERENCE TO SEQUENCE LISTING

This application contains a Sequence Listing submitted as an electronic text file named "Sequence_Listing_ST25.txt", having a size in bytes of 34 kb, and created on Feb. 27, 2017. The information contained in this electronic file is hereby incorporated by reference in its entirety pursuant to 37 CFR §1.52(e)(5).

FIELD OF THE INVENTION

The invention relates generally to disease diagnostics and therapeutics, and in particular to methods for detecting infection of anthrax or treating or preventing anthrax infection in a patient and screening anthrax therapeutics.

BACKGROUND OF THE INVENTION

Anthrax is caused by infection with *Bacillus anthracis*, a spore-forming, rod-shaped bacterium. The dormant spore-form is highly resistant to extreme conditions, high temperatures, and a variety of chemical treatments. The spores gain entry either through an open wound, causing cutaneous disease, or by ingestion, causing gastrointestinal disease or are inhaled causing inhalation anthrax. All three forms can progress to a systemic infection leading to shock, respiratory failure, and death. (Mock, M. and Mignot, T. (2003), *Cell Microbiol.*, 5(1):15-23). The stability of the spores and their infectious capacity make them a convenient bioterrorist weapon.

The two known toxins of *B. anthracis* are binary combinations of protective antigen (PA), named for its ability to induce protective immunity against anthrax, with either edema factor (EF) or lethal factor (LF). PA is the cell binding component of both toxins and is responsible for bringing the catalytic EF or LF into the host cells. EF is an adenylate cyclase that converts ATP to cyclic AMP and causes edema (Brossier, F. and Mock, M. (2001), *Toxicon.* 39(11):1747-55). The combination of PA-EF forms edema toxin (ETx) which causes edema when injected locally. LF is a zinc-dependent endoprotease known to target the amino-terminus of the mitogen-activated protein kinase kinase (MAPKK) family of response regulators (Id.). The cleavage of these proteins disrupts a signaling pathway and leads to cytokine dysregulation and immune dysfunction. LF combined with PA forms lethal toxin (LTx), which is lethal when injected on its own. It is also known that there are fatal anthrax cases where administration of antibiotics and clearance of bacteria have failed to rescue the patient. This indicates that there may be a "point of no return" level of LTx in the blood that may predict the outcome of infection. Clearly, LTx and its components are important targets for diagnostics and quantification.

Assays for EF activity such as competitive enzyme assays (Duriez, E, et al., *Anal. Chem.*, 2009; 81:5935-5941) or radiometric assays (Gottle, M, et al., *Biochemistry*, 2010; 49:5494-503), are impractical for high-throughput screening of compound collections and rapid diagnosis of host infection. Methods for rapid screening of patients in a hospital setting or identification of potent and selective EF inhibitors requires an assay that is less labor intensive, has faster turnaround, and is effective at low levels of enzyme.

Development of targeted therapies following anthrax infection is essential to managing a patient population. As such, there exists a need for compositions and methods that can be used as aids in a screening assay for identification and development of inhibitors of anthrax toxin activity or for identifying active LF such as in the circulation of a subject.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Provided are peptide sequences that represent an epitope sequence in *B. anthracis* lethal factor that when recognized by the provided antibodies, illustratively AVR1674 (LFG2 3F3:3H9:2C10:4B10) and AVR1675 (LFG2 3F3:3H9:2C10:3D10), produces stimulation of lethal factor activity. A peptide is or includes a peptide sequence included in the consensus sequence (T/S)-$X_1$-(K/R)-(D/E), optionally, (T/S)-$X_1$-(K/R)-(D/E)-$X_2$-$X_3$. It has been demonstrated that peptides having the consensus sequence are specifically recognized by the provided antibodies that will enhance LF activity.

In some aspects an antibody recognizes a consensus sequence as above where, $X_1$ is phenylalanine, alanine, or histidine. In some aspects, the amino acid at position 4 is glutamate. In some aspects, $X_3$ is isoleucine or alanine. It is appreciated that these and other aspects, may be combined in any way. Optionally, the provided antibodies recognize the epitope with a sequence that is or includes the sequence of TFKDEI (SEQ ID NO: 4), optionally THQDEIFEQK (SEQ ID NO: 41).

An antibody that recognizes the an epitope sequence as per that provided herein includes a complementarity determining region including or limited to the sequence selected from the group consisting of SEQ ID NO: 48, SEQ ID NO: 49, SEQ ID NO: 50, SEQ ID NO: 51, SEQ ID NO: 52, and SEQ ID NO: 53. In some aspects, and antibody includes a heavy chain that includes the sequence of SEQ ID NOs: 42, 43, or 44 as one or more CDR regions. In some aspects, the antibody includes a light chain that includes the sequence of SEQ ID NOs: 45, 46, or 47 as one or more CDR regions. An antibody is optionally a chimeric antibody, optionally a humanized antibody, optionally derived from a mouse background, or a human antibody including one or more of the CDR sequences of SEQ ID NOs: 42-47. In some aspects, an antibody is a chimeric or humanized antibody that includes the a sequence of SEQ ID NO: 48, SEQ ID NO: 49, SEQ ID NO: 50, SEQ ID NO: 51, SEQ ID NO: 52, of SEQ ID NO: 53.

It is another object to provide a process of enhancing *B. anthracis* lethal factor activity either in vitro or in vivo including combining *B. anthracis* lethal factor or an active fragment thereof with an antibody that specifically recognizes an peptide having a sequence included in the sequence (T/S)-$X_1$-(K/R)-(D/E)-$X_2$-$X_3$ or specifically recognizes the epitope in lethal factor that is or includes the sequence of THQDEIYEQV (SEQ ID NO. 1). The combination of LF with an antibody is optionally in an aqueous medium. Optionally, the medium includes an antibody that recognizes an epitope including or limited to the sequence of THQDEIFEQK (SEQ ID NO: 41), or portion thereof. In a process, an antibody is optionally AVR 1674, AVR 1675, or combinations thereof.

BRIEF DESCRIPTION OF THE DRAWINGS

FIG. 4A illustrates a concentration dependent activation of LF by antibody AVR1674;

FIG. 4B illustrates a concentration dependent activation of LF by antibody AVR1675;

FIG. 5 illustrates the sequence alignments of heavy chains of antibodies capable of enhancing LF or LTx activity;

FIG. 6 illustrates the sequence alignments of light chains of antibodies capable of enhancing LF or LTx activity;

FIG. 7 illustrates sequence alignments of heavy chain antibody nucleotide and amino acid sequences of an exemplary antibody to a standard mouse comparator;

FIG. 8 illustrates sequence alignments of light chain antibody nucleotide and amino acid sequence to a standard mouse comparator.

DETAILED DESCRIPTION OF EMBODIMENTS OF THE INVENTION

Figure 1:
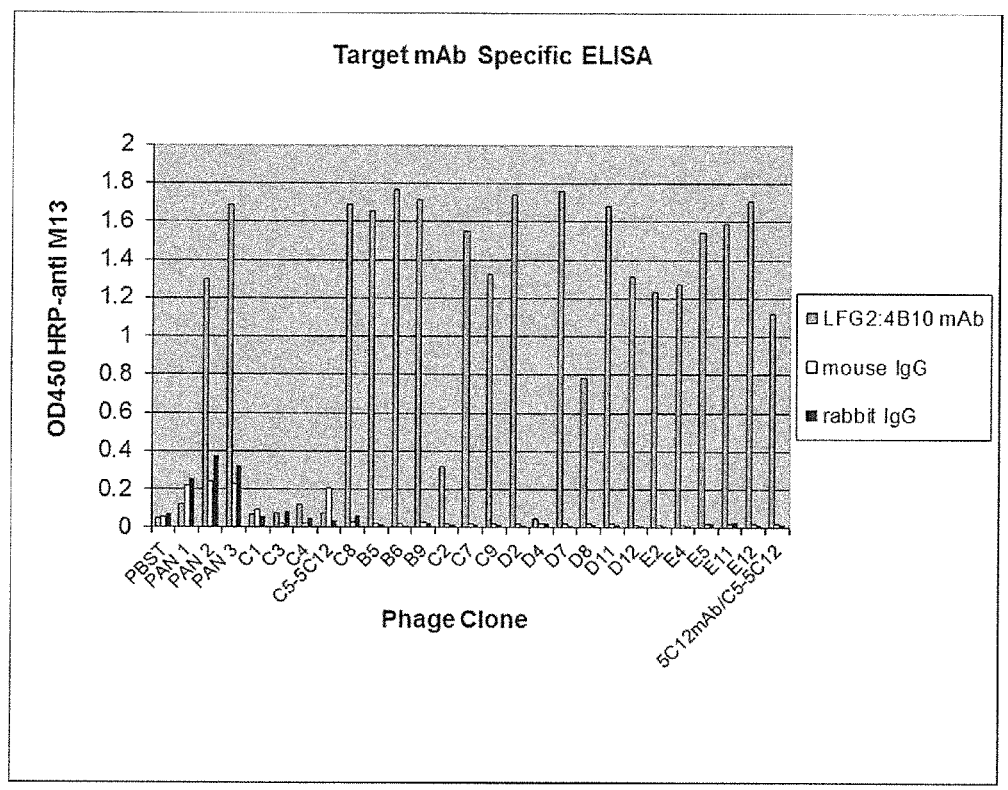
FIG. 1 is a summary of ELISA results from peptides having sequences identified in phage display analyses illustrating high affinity binding (defined as an O.D. of 0.5 or greater) for many sequences.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the process is described as an order of individual steps or using specific materials, it is appreciated that described steps or materials may be interchangeable such that the description of the invention includes multiple parts or steps arranged in many ways as is readily appreciated by one of skill in the art.

A recent mass spectrometry assay was developed using antibodies that specifically target *Bacillus anthracis* lethal factor (LF) without neutralizing the levels of LF in an organism or reducing the activity of LF in an assay system. Boyer et al., *Anal. Chem.*, 2007; 79 (22):8463-8470. The inventors discovered that two monoclonal antibodies useful in this assay, AVR1674 and AVR1675, enhance LF activity. The invention has utility to aid in the identification and development of therapeutics for the treatment or prevention of *Bacillus anthracis* infection, or as a composition useful for the screening or other detection of *Bacillus anthracis* lethal factor (LF) in a sample.

The inventors discovered that antibody AVR1674 and AVR1675 recognize a particular epitope in LF leading to stimulation of LF activity indicating that modulation of this region by antibody interactions may detract from the effectiveness of vaccines or naturally derived immune responses to the presence of LF in the circulation. The epitope was determined by significant effort to include the sequence THQDEIYEQV (SEQ ID NO. 1), which represents residues 677-686 of the immature full length LF protein as found at Swiss-Prot Accession No: P15917 and SEQ ID NO: 2, and in particular the first six residues of SEQ ID NO:1.

```
                                                             (SEQ ID NO: 2)
   1    mnikkefikv ismsclvtai tlsgpvfipl vqgagghgdv gmhvkekekn kdenkrkdee 61    rnktqeehlk eimkhivkie vkgeeavkke aaekllekvp sdvlemykai ggkiyivdgd 121    itkhisleal sedkkkikdi ygkdallheh yvyakegyep vlviqssedy ventekalnv 181    yyeigkilsr dilskinqpy qkfldvinti knasdsdgqd llftnqlkeh ptdfsvefle 241    qnsnevqevf akafayyiep qhrdvlqlya peafnymdkf neqeinlsle elkdqrmlar 301    yekwekikqh yqhwsdslse egrgllkklq ipiepkkddi ihslsqeeke llkriqidss 361    dflsteekef lkklqidird slseeekell nriqvdssnp lsekekeflk klkldiqpyd 421    inqrlqdtgg lidspsinld vrkqykrdiq nidallhqsi gstlynkiyl yenmninnIt 481    atlgadlvds tdntkinrgi fnefkknfky sissnymivd inerpaldne rlkwriqlsp 541    dtragyleng klilqrnigl eikdvqiikq sekeyirida kvvpkskidt kiqeaqlnin
```

```
601    qewnkalglp  kytklitfnv  hnryasnive  saylilnewk  nniqsdlikk  vtnylvdgng 661    rfvftditlp  niaeqythqd  eiyeqvhskg  lyvpesrsil  lhgpskgvel  rndsegfihe 721    fghavddyag  ylldknqsdl  vtnskkfidi  fkeegsnits  ygrtneaeff  aeafrlmhst 781    dhaerlkvqk  napktfqfin  dqikfiins
```

For anthrax toxin LF the mature secreted protein (776 aa; $M_r$ 90237) is preceded by a 33-aa signal peptide (Bragg and Robertson, *Gene.* 1989 Sep. 1; 81(1):45-54), which is included in the above sequence for immature LF. Mature LF, therefore, has this signal sequence removed and the numbering adjusted accordingly.

A peptide for use in reducing antibody enhanced LTx or LF activity includes the amino acid consensus sequence (T/S)-$X_1$-(K/R)-(D/E)-$X_2$-$X_3$ wherein $X_1$ is any amino acid, optionally phenylalanine, alanine, or histidine. In some embodiments, a peptide has a sequence (T/S)-$X_1$-(K/R)-(D/E)-$X_2$-$X_3$ where: $X_1$ is any amino acid, optionally phenylalanine, alanine, or histidine; $X_2$ is any amino acid, optionally aspartic acid or glutamic acid; and $X_3$ is any non-polar or hydrophobic amino acid, optionally isoleucine or alanine. The amino acid sequence (T/S)-$X_1$-(K/R)-(D/E) is optionally used alone or as part of a larger peptide that encompasses an epitope for a stimulatory antibody. Optionally, the sequence (T/S)-$X_1$-(K/R)-(D/E) is attached to a linker peptide. A linker peptide is optionally attached to the C-terminal. In some embodiments, a linker peptide has the sequence GGGSK (SEQ ID NO: 3). A peptide has from 4 to 100 amino acids, or any value or range therebetween. A peptide optionally has 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amino acids as long as the sequence (T/S)-$X_1$-(K/R)-(D/E), optionally (T/S)-$X_1$-(K/R)-(D/E)-$X_2$-$X_3$, is present in the peptide. In some embodiments, a peptide includes the sequence TFKDEI (SEQ ID NO: 4) or variants thereof. In some embodiments, a variant is a peptide that includes the sequence (T/S)-$X_1$-(K/R)-(D/E)-$X_2$-$X_3$ wherein: the amino acids at position P1, P3 and P4 are essential and limited as described; $X_1$ is preferably F, A, or H with preference in that order; the amino acid at $X_2$ is preferably E; or the amino acid at position $X_3$ is preferably A. Optionally, a peptide does not have the wild type sequence THQDEIYEQV (SEQ ID NO. 1) or a wild type fragment thereof absent a non-wild type sequence amino acid within or attached to the peptide, or the presence of an other non-wild type element(s).

A peptide as defined herein includes variants that are conservative substitutions of desirable amino acids. Illustratively, a variant is a conservative substitution of residues in (T/S)-$X_1$-(K/R)-(D/E) at P2, or (T/S)-$X_1$-(K/R)-(D/E)-$X_2$-$X_3$ at P2, P5, or P6, that may or may not be the substitutions listed above. A conservative amino acid substitution is recognized by one of skill in the art.

Also provided is an immunogen for use as a vaccine for prophylaxis or treatment of anthrax infection. An immunogen is a peptide or protein corresponding one or more regions of LF according to SEQ ID NO: 2, the mature LF sequence, or a variant thereof, that does not include a L2 region in domain IV including the sequence (T/S)-$X_1$-(K/R)-(D/E). An immunogen, therefore, capitalizes on the recognition that the sequence (T/S)-$X_1$-(K/R)-(D/E) is a minimal epitope conserved region for antibody enhancement of LF activity. By eliminating or altering this sequence of LF, the molecule or portion thereof can be used as a superior vaccine to protect against the effects of anthrax infection by reducing or eliminating the likelihood of natural development of LF activity enhancing antibodies. This region of LF that is to be excluded or altered in an immunogen maps to the L2 region of the catalytic domain IV of LF and forms a solvent exposed loop. Immunization of a subject with an inventive immunogen or nucleic acid sequence encoding this immunogen will elicit an immune response in the subject leading to toxin neutralization and reduction or elimination of undesirable affects of *Bacillus anthracis* infection while reducing or eliminating the risk of developing a LF activity enhancing antibody.

An immunogen as defined herein includes one or more amino acids of domain IV in LF on each side of the sequence of residues 677-680 in the L2 loop as found in SEQ ID NO: 2, or conservative mutations thereof, but need not be the residues immediately adjacent to residues 677-680. As such, an immunogen includes both N- and C-terminal amino acids representative of LF that flank residues 677-680, the L2 sequence, or any portion of the L2 sequence excluding the residues 677-680, but need not be immediately adjacent thereto. It is appreciated that these residues may, but are not required to in some embodiments, possess the residues of SEQ ID NO: 2 immediately adjacent to the L2 loop, but will include 3 or more amino acids that are found on each side of any deleted portion of the L2 loop in domain IV of LF, or conservative mutations thereof. As such, an immunogen includes at minimum 6 amino acids representing at least portions of domain IV of LF that exclude one or more amino acids of the sequence (T/S)-$X_1$-(K/R)-(D/E). Specific examples of an immunogen are LF domain IV deletions of SEQ ID NO: 2 with a deletion of residues 677-680, 677-686, or any portion or the whole of residues 667-688 representing the L2 region that includes residues 677-680. Illustrative examples of a deletion mutation include deletion of one or more residues of the sequence (T/S)-$X_1$-(K/R)-(D/E) representing residues 677-680 of SEQ ID NO: 2, optionally, the amino acid at P1, P3, P4, or combinations thereof are deleted.

An immunogen is optionally a portion of LF that includes amino acid sequences from the two regions that flank residues 677-680, 677-686, or any portion or the whole of residues 667-688 representing the L2 region that excludes residues 677-680. Illustratively, an immunogen includes all or a portion of LF domain I, II, III, or IV, and also includes amino acid sequences from the two regions that flank residues 677-680, 677-686, or any portion or the whole of residues 667-688 representing the L2 region that excludes residues 677-680. Illustrative examples of an immunogen and methods of immunogen preparation are described in Quinn et al., *J. Biol. Chem.,* 1991; 266:20124-20130. The structure of LF and location of the L2 region in domain IV and its proximity to the LF active site are found in Dalkas, et al., *Protein Science,* 2009; 18: 1774-1785.

Optionally, an immunogen includes the L2 region with a substitution within the sequence (T/S)-$X_3$-(K/R)-(D/E) where P1 is neither T nor S, P3 is neither K nor R, P4 is neither D nor E, or combinations thereof. One or more essential residues in the consensus sequence (T/S)-$X_1$-(K/R)-(D/E) is substituted by an alanine, glycine, or other amino acid resulting in a sequence that is not recognized by a LF function enhancing antibody such as AVR1674 and AVR1675.

In some aspects, vaccines are provided alone or in combination with a carrier, adjuvant, or other component that, when administered to a subject such as a human or other animal, induces the production of antibodies that recognize LF without recognition of residues 677-680 of SEQ ID NO: 2. Immunization is achieved by administering to a subject an immunogenic amount of one or more of the immunogens in a pharmaceutically acceptable carrier. An immunogenic amount is any amount that will produce an immunological response, illustratively the production of antibodies, in a subject to which the immunogen is administered.

As used herein, the terms "subject" or "organism" are treated synonymously and are defined as any organism capable of hosting infection of bacteria, illustratively *Bacillus anthracis*. A subject illustratively includes: any mammal such as humans, non-human primates, horses, goats, cows, sheep, pigs, dogs, cats, rodents; as well as cells. In some embodiments, a subject is a human and excludes other organisms. In some embodiments, a subject is a cell and is exclusive of an organism.

A therapeutically effective amount is defined as an amount of a compound that when administered to a subject, will reduce enhancement of LF activity at any measurable level. When a molecule is administered as an immunogen, an effective amount is any amount that will produce one or more immune responses in a subject, where an immune response is a response recognized in the art as expected.

The terms "biologically active peptide" and "peptide therapeutic agent," "peptide," "polypeptide," "protein", and "immunogen" are used herein and are intended to mean a natural or synthetic compound containing 4 or more amino acids. It is appreciated that a "nucleic acid immunogen" as used herein includes one or more nucleic acids. It is further appreciated that the description of elements of a peptide are also appreciated as corresponding to description of an immunogen that is not a nucleic acid immunogen. Amino acids present in a peptide include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, alto-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylomithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. Accordingly, the "peptide" as used herein may include peptides having between 4 and about 1000 amino acids or having a molecular weight in the range of about 150-350,000 Daltons.

Modifications and changes can be made in the sequence of a peptide and still obtain a molecule capable of reducing enhancement of LF activity. For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 are optional, those within +1 are optional preferred, and those within +0.5 are optional.

Substitution of like amino acids can also be made on the basis of hydrophilicity, particularly, where the biological functional equivalent polypeptide or peptide thereby created is intended. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an activity equivalent or superior peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Such substitutions are typically considered conservative substitutions. Exemplary conservative substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gin: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a peptide as set forth above. In particular, embodiments of the polypeptides can include variants having about 50%, 60%, 70%, 80%, 90%, and 95% sequence identity to the polypeptide of interest.

A peptide is obtained by any of various methods known in the art illustratively including isolation from a cell or organism, chemical synthesis, expression of a nucleic acid and partial hydrolysis of proteins. Chemical methods of peptide synthesis are known in the art and include solid phase peptide synthesis and solution phase peptide synthesis for instance. A peptide included in an inventive composition may be a naturally occurring or non-naturally occurring peptide. The term "naturally occurring" refers to a peptide endogenous to a cell, tissue or organism and includes allelic variations. A non-naturally occurring peptide is synthetic or produced apart from its naturally associated organism or modified and is not found in an unmodified cell, tissue or organism.

As used herein, the term "sample" is defined as a sample obtained from a biological organism, a tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial fluid, cerebrospinal fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, water, air, gas, powder, soil, biological waste, feces, cell culture media, cytoplasm, cell releasate, cell lysate, buffers, or any other fluid or solid media.

A peptide is illustratively recombinant. An inventive peptide may be co-expressed with associated tags, modifications, other proteins such as in a fusion peptide, or other modifications or combinations recognized in the art. Illustrative tags include 6×His, FLAG, biotin, ubiquitin, SUMO, or other tag known in the art. A tag is illustratively cleavable such as by linking to a peptide via an enzyme cleavage sequence that is cleavable by an enzyme known in the art illustratively including, but not limited to Factor Xa, thrombin, SUMOstar protein as obtainable from Lifesensors, Inc., Malvern, Pa., or trypsin. It is further appreciated that chemical cleavage is similarly operable with an appropriate cleavable linker.

Peptide expression is illustratively accomplished from transcription of nucleic acid sequence encoding a peptide and translation of RNA transcribed from the nucleic acid sequence. Peptide expression is optionally performed in a cell based system such as in E. coli, Hela cells, or Chinese hamster ovary cells. It is appreciated that cell-free expression systems are similarly operable.

It is recognized that numerous variants, including analogues or homologues, are within the scope of a peptide as defined herein according to some embodiments including amino acid substitutions, alterations, modifications, or other amino acid changes that increase, decrease, or do not alter the function of the ability of peptide to reduce or eliminate antibody induced enhancement of LF or LTx activity. It is appreciated that a variant includes one or more amino acid insertions, deletions, substitutions, or modifications.

Further aspects of the present disclosure concern the purification, otherwise termed isolation, and in particular embodiments, the substantial purification, of an encoded peptide, immunogen, or antibody. The term "purified" or "isolated" as used herein, is intended to refer to a composition, isolatable from other components, wherein the composition is purified to any degree relative to its naturally-obtainable state or state as expressed in a cell or synthetic system. A purified immunogen or peptide, therefore, also refers to a protein or peptide, free from the environment in which it may naturally occur.

Generally, "purified" or "isolated" will refer to a protein (including an antibody), or peptide composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure as based on knowledge in the art. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein or peptide purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a peptide can vary, sometimes significantly, with different conditions of SDS/PAGE (Capaldi et al., *Biochem. Biophys. Res. Comm.,* 76:425, 1977). It will therefore be appreciated that under differing electrophoresis conditions, the apparent molecular weights of purified or partially purified expression products may vary.

Isolation of a peptide is included in some embodiments. Methods of peptide isolation illustratively include column chromatography, affinity chromatography, gel electrophoresis, filtration, or other methods known in the art. In some embodiments, peptide is expressed with a tag operable for affinity purification. A preferred tag is a 6×His tag. A 6×His tagged inventive protein is illustratively purified by Ni-NTA column chromatography or using an anti-6×His tag antibody fused to a solid support. (Geneway Biotech, San Diego, Calif.) Other tags and purification systems are similarly operable.

It is appreciated that a peptide or antibody is optionally not tagged. In such embodiments purification is optionally achieved by methods known in the art illustratively including ion-exchange chromatography, affinity chromatography, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

A peptide or antibody is illustratively recombinant. A peptide or antibody may be co-expressed with associated tags, modifications, other proteins such as in a fusion peptide, or other modifications or combinations recognized in the art. Illustrative tags include 6×His, FLAG, biotin, ubiquitin, SUMO, or other tag known in the art. A tag is illustratively cleavable such as by linking to PA immunogen or an associated protein via an enzyme cleavage sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

Protein expression is illustratively accomplished from transcription of PA immunogen or antibody nucleic acid sequence, translation of RNA transcribed from PA or antibody nucleic acid sequence, modifications thereof, or fragments thereof. Protein expression is optionally performed in a cell based system such as in *E. coli*, Hela cells, or Chinese hamster ovary cells. It is appreciated that cell-free expression systems are similarly operable.

A peptide or antibody is optionally chemically synthesized. Methods of chemical synthesis have produced proteins greater than 600 amino acids in length with or without the inclusion of modifications such as glycosylation and phosphorylation. Methods of chemical protein and peptide synthesis illustratively include solid phase protein chemical synthesis. Illustrative methods of chemical protein synthesis are reviewed by Miranda, L P, *Peptide Science,* 2000, 55:217-26 and Kochendoerfer G G, *Curr Opin Drug Discov Devel.* 2001; 4(2):205-14.

A peptide is optionally characterized by measurements including, without limitation, western blot, macromolecular mass determinations by biophysical determinations, SDS-PAGE/staining, HPLC and the like, antibody recognition assays, cell viability assays, apoptosis assays, assays for the activity of LF or LTx such as those described by Boyer et al., *Anal. Chem.,* 2007; 79 (22):8463-8470, and assays to infer immune protection or immune pathology by adoptive transfer of cells, proteins or antibodies.

Also provided are isolated polynucleotides encoding a peptide that reduces or eliminates antibody enhancement of LF or LTx, or that encode an immunogen, or that encode an antibody or fragments thereof. These polynucleotides can be used to produce the peptides or antibodies. It is appreciated that the degenerate nucleic acid code is well understood such that one of skill in the art fully and immediately understands a nucleic acid sequence that will produce a desired peptide sequence.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" or "polynucleotide" refers to multiple nucleotides attached in the form of a single or double stranded molecule that can be natural, or derived synthetically, enzymatically, and by cloning methods. The term "oligonucleotide" refers to a polynucleotide of less than 200 nucleotides. The terms "nucleic acid" and "oligonucleotide" may be used interchangeably in this application.

A polynucleotide as used herein refers to single- or double-stranded molecules that may be DNA, including of the nucleotide bases A, T, C and G, or RNA, comprised of the bases A, U (substitutes for T), C, and G. The nucleic acid may represent a coding strand or its complement. Nucleic acids may be identical in sequence to the sequence naturally occurring or may include alternative codons that encode the same amino acid as that found in the naturally occurring sequence. Furthermore, nucleic acids may include codons that represent conservative substitutions of amino acids as are well known in the art.

The nucleic acid encoding the peptide of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a peptide and/or polypeptide of this invention.

The present invention also provides a vector with a nucleic acid sequence encoding peptide or antibody sequence, sequences, or portions thereof therein. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

An inventive nucleic acid sequence is provided. A nucleic acid sequence optionally encodes a peptide of SEQ ID NO: 1, SEQ ID NO: 2, SEQ ID NO: 3, other sequences herein, fragments thereof, or variants thereof such as immunogens and other peptides as described herein. The genetic code is a degenerate code whereby specific nucleic acid sequences encode for particular amino acids. As such it is well within the level of those of skill in the art to determine a nucleic acid sequence that will encode the inventive peptides.

The inventive nucleic acid sequence is optionally isolated from the cellular materials with which it is naturally associated. As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids is optionally accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cells systems known in the art as amendable to transfection and nucleic acid and/or protein expression. Methods of nucleic acid isolation are similarly recognized in the art. Illustratively, plasmid DNA amplified in *E. coli* is cleaved by suitable restriction enzymes such as NdeI and XhoI to linearize DNA. The DNA is subsequently isolated following gel electrophoresis using a S.N.A.P.™ UV-Free Gel Purification Kit (Invitrogen, Carlsbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The nucleotide sequences of the invention may be isolated by conventional uses of polymerase chain reaction or cloning techniques such as those described in conventional texts. For example, the nucleic acid sequences of this invention may be prepared or isolated from DNA using DNA primers and probes and PCR techniques. Alternatively, the inventive nucleic acid sequence may be obtained from gene banks derived from *Bacillus anthracis* whole genomic DNA. These sequences, fragments thereof, modifications thereto and the full-length sequences may be constructed recombinantly using conventional genetic engineering or chemical synthesis techniques or PCR, and the like.

Also provided is a vector with a nucleic acid sequence encoding an immunogen or other peptide sequence therein. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

Also provided is a host cell transformed with an appropriate vector or with the inventive peptide sequence. Illustrative host cells include *E. coli* or Sf9 cells. Optionally, cell transfection is achieved by electroporation.

Recombinant or non-recombinant proteinase peptides or recombinant or non-recombinant proteinase inhibitor peptides or other non-peptide proteinase inhibitors can also be used in the present invention. Proteinase inhibitors are optionally modified to resist degradation, for example degradation by digestive enzymes and conditions. Techniques for the expression and purification of recombinant proteins are known in the art (see Sambrook Eds., Molecular Cloning: A Laboratory Manual $3^{rd}$ ed. (Cold Spring Harbor, N.Y. 2001).

Some embodiments of the present invention are compositions containing nucleic acid sequences that can be expressed as encoded peptides. The engineering of DNA segment(s) for expression in a prokaryotic or eukaryotic system may be performed by techniques generally known to those of skill in recombinant expression. It is believed that virtually any expression system may be employed in the expression of the claimed nucleic acid and amino acid sequences.

Generally speaking, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene.

As used herein, the terms "engineered" and "recombinant" cells are synonymous with "host" cells and are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. Engineered cells are cells having a gene or genes introduced through the hand of man. Recombinant cells include those having an introduced cDNA or genomic DNA, and also include genes positioned adjacent to a promoter not naturally associated with the particular introduced gene.

To express a recombinant encoded polypeptide in accordance with the present invention one would prepare an expression vector that comprises a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* .chi. 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk−, hgprt− or aprt− cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

It is contemplated that the isolated nucleic acids of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

A nucleic acid of this invention can be in a cell, which can be a cell expressing the nucleic acid whereby a peptide and/or polypeptide of this invention is produced in the cell. In addition, the vector of this invention can be in a cell, which can be a cell expressing the nucleic acid of the vector whereby a peptide and/or polypeptide of this invention is produced in the cell. It is also contemplated that the nucleic acids and/or vectors of this invention can be present in a host animal (e.g., a transgenic animal) which expresses the nucleic acids of this invention and produces the peptides and/or polypeptides of this invention.

The nucleic acid encoding the peptides and polypeptides of this invention can be any nucleic acid that functionally encodes the peptides and polypeptides of this invention. To functionally encode the peptides and polypeptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Expression control sequences useful include promoters derived from metallothionine genes, actin genes, immunoglobulin genes, CMV, SV40, adenovirus, bovine papilloma virus, etc. A nucleic acid encoding a selected peptide or polypeptide can readily be determined based upon the genetic code for the amino acid sequence of the selected peptide or polypeptide and many nucleic acids will encode any selected peptide or polypeptide. Modifications in the nucleic acid sequence encoding the peptide or polypeptide are also contemplated. Modifications that can be useful are modifications to the sequences controlling expression of the peptide or polypeptide to make production of the peptide or polypeptide inducible or repressible as controlled by the appropriate inducer or repressor. Such methods are standard in the art. The nucleic acid of this invention can be generated by means standard in the art, such as by recombinant nucleic acid techniques and by synthetic nucleic acid synthesis or in vitro enzymatic synthesis.

Also provided are antibodies that enhance LT activity, LTx activity, or both in an assay system. An illustrative example of one such antibody is discussed in Boyer et al., *Anal. Chem.*, 2007; 79 (22):8463-8470. A specific illustrative example of an activity enhancing antibody is AVR1674. Antibodies with the activity of AVR1674 are particularly preferred. One of ordinary skill in the art understands how to produce antibodies by standard techniques and screen the resulting monoclonal or polyclonal antibodies for their ability to interact with an epitope sequence. Such methods are illustratively taught by Monoclonal Antibodies: Methods and Protocols, Albitar, M, ed., Humana Press, 2010 (ISBN 1617376 los, E, and Lane, D. eds., Cold Spring Harbor Laboratory Press, 1988 (ISBN-10: 0879693142).

Antibodies that enhance LF or LTx activity as provided herein are capable of specifically binding to a peptide or to LT or LTx are useful as research tools, clinical diagnostic assay components, or other uses. An antibody optionally is used as a screening agent for the presence or absence of LT or LTx in a sample. For example, an antibody enhances LT or LTx activity toward a particular substrate for the LT or LTx. This allows for detection of lower amounts of LT or LTx in a sample than would otherwise be achievable. The terms "antibody" and "antibodies" as used herein include monoclonal antibodies, polyclonal, chimeric, single chain, bispecific, simianized, and humanized antibodies, as well as Fab fragments, including the products of a Fab immunoglobulin expression library. The term "antigen" refers to the LT protein or any portion of the LT protein that includes residues 677-682 of immature LT protein. One particular example of an antibody suitable for use in processes for detecting LT or screening for LT activity is AVR1674 or AVR1675 (Boyer et al., *Anal. Chem.,* 2007; 79 (22):8463-8470).

An antibody that enhances LF or LTx activity includes two heavy chains and optionally two light chains. Each of the heavy chains and light chains includes three complementarity determining regions (CDRs) separated and flanked by framework regions. A heavy chain optionally includes or is a sequence of: TGEAWGFIEVQLHESGAELVKPGASVRLSCKASGYTFTSYYIYWVKQRPGQGLEWIGDI NPSDGDTDFNEKFKSKATLTVDKSSSTAYMQLSSLTSEDSAVYYCTRSRGGFAY WGQG TLVTVSAAKTTPPSVYPLAPGSAAQTNSMVTLGCLVKGYFPEPVTVTWNSGSL (SEQ ID NO: 42). In some aspects, a heavy chain includes or is a sequence of: EVQLQVSGAELVKPGASVRLSCKASGYTFTSYYIYWVKQRPGQGLEWIGDINPSDGDTD FNEKFKSKATLTVDKSSSTAYMQLSSLTSEDSAVYYCTRSRGGFAYWGQGTLVTVSAA KTTPPSVYPLAPGSAAQTNSMVTLGCLVKGYFPEPVTVTWNSGS (SEQ ID NO: 43). In some aspects, a heavy chain includes or is a sequence of: VQLQESGAELVKPGASVRLSCKASGYTFTSYYIYWVKQRPGQGLEWIGDINPSDGDTDF NEKFKSKATLTVDKSSSTAYMQLSSLTSEDSAVYYCTRSRGGFAYW GQGTLVTVSAAK TTPPSVYPLAPGSAAQTNSMVTLGCLVKGYFPEPVTVTWNSGS (SEQ ID NO: 44). The heavy chains of SEQ ID NOs: 42 and 43 are believed attributable to AVR 1674. The heavy chain of SEQ ID NO: 44 is believed attributable to AVR 1675. The heavy chain sequences of each of these sequences are similar. FIG. 5 illustrates a sequence alignment of the various heavy chains.

In some aspects, a heavy chain includes a substitution at any of one or more positions in SEQ ID NO: 42, 43, or 44. Optionally, a residue three residues C-terminal to the first valine in any one or more of SEQ ID NO: 42, 43, or 44 is substituted to a Q or H. In some aspects, a residue three residues C-terminal to the first valine in any one or more of SEQ ID NO: 42, 43, or 44 is substituted to any natural or synthetic amino acid. Optionally, a residue three residues C-terminal to the first valine in any one or more of SEQ ID NO: 42, 43, or 44 is alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, 2-naphthylalanine, or optionally any other natural or synthetic amino acid.

An antibody that enhances LF or LTx activity optionally includes two light chains. A light chain optionally includes or is a sequence of: ISSRSSQSIVHSNGNTYLEWYLQKPAQSPKLLIFKVSNRFSGVPDRFSRSGSGTDFTLKISR VEAEDLGIYYCFQGSHVPWTF (SEQ ID NO: 45). A light chain optionally includes or is a sequence of: SHGDQASISSRSSQSIVHSNGNTYLEWYLQKPAQSPKLLIFKVSNRFSGVPDRFSRSGSGT DFTLKISRVEAEDLGIYYCSQGSHVPWTFGGGTKL (SEQ ID NO: 46). A light chain optionally includes or is a sequence of: ISSRSSQSAVHSNGNTYLEWYRRNPAQSPKLLIIKVSNRFSGVPDRFSHSGSGTDFTLKIS RVEAEDLGIYYCFQGSHV (SEQ ID NO: 47). The light chains of SEQ ID NOs: 45 and 46 are believed attributable to AVR 1674. The light chain of SEQ ID NO: 47 is believed attributable to AVR 1675. FIG. 6 illustrates a sequence alignment of the various light chains.

In some aspects, an antibody includes one or more of the framework regions (FR) or one or more of the complementarity determining regions (CDR) included in any one or more of SEQ ID NOs: 42 to 47. Typical antibodies include two heavy chains and two light chains. The association of the chains forms a full antibody that include a variable Fab region and a constant Fc portion that is formed from the heavy chains alone. The Fab region includes variable domains on each of the heavy and light chains. Antibody specificity is conferred by the resulting sequence of particular regions of these variable domains known as the CDRs. Each heavy chain and each light chain includes 3 CDRs separated by much more conserved FRs. The sequences of these CDRs, particularly CDR1 and CDR2 in the present antibodies, confer the antigen specificity and binding affinity. As such, the most relevant portions of an antibody as provided herein are the presence of one or more of the CDRs in one or more of SEQ ID NOs: 42 to 47.

In some aspects, an antibody includes one or more heavy chain CDRs of SEQ ID NOs: 42 to 44. Optionally, an antibody includes a CDR having or including the sequence of YTFTSYY (SEQ ID NO: 48). In some aspects, an antibody includes a CDR having or including the sequence of INPSDGDT (SEQ ID NO: 49). In some aspects, an antibody includes a CDR having or including the sequence of TRSRGGFAY (SEQ ID NO: 50). In some aspects, a heavy chain includes two or more of any one or more of the CDRs of SEQ ID NOs: 48 to 50. Optionally, an antibody includes each of the CDRs of SEQ ID NOs: 48 to 50. Optionally, an antibody includes each of the CDRs of SEQ ID NOs: 48 to 50 and the FRs separating the CDRs in any one of SEQ ID NOs: 42 to 44.

In some aspects, an antibody includes one or more of the light chain CDRs of SEQ ID NOs: 45 to 47. Optionally, an antibody includes a CDR having or including the sequence of QSIVHNSGNTYL (SEQ ID NO: 51). Optionally, an antibody includes a CDR having or including the sequence of KVS (SEQ ID NO: 52). Optionally, an antibody includes a CDR having or including the sequence of FQGSHVP (SEQ ID NO: 53). In some aspects, a light chain includes two or more of any one or more of the CDRs of SEQ ID NOs: 51 to 53. Optionally, an antibody includes each of the CDRs of SEQ ID NOs: 51 to 53. Optionally, an antibody includes each of the CDRs of SEQ ID NOs: 51 to 53 and the FRs separating the CDRs in any one of SEQ ID NOs: 45 to 47.

The variable regions of SEQ ID NOs: 42 to 47 are optionally included in an antibody in whole or in part. An antibody is optionally a mouse antibody, or a mouse/human chimeric antibody such as an antibody that has been humanized as understood in the art. In some aspects, the variable regions of SEQ ID NOs: 42 to 44 are optionally included in a mouse antibody, optionally an antibody of the IGHV1S81*02 type, optionally as found at UniProt accession no: Q99LC4 and SEQ ID NO: 54. In some aspects, a heavy chain background is encoded within a background that is the Musmus IGHV1S81*02 for the V allele or Musmus IGHJ3*01 F for the J allele, or combinations thereof. A light chain variable region of SEQ ID NOs: 45-47 are optionally included in a mouse antibody, optionally of the IGKV1S81 type as found at NCBI accession no: AF304547 and SEQ ID NO: 55. In some aspects, the light chain background is Musmus IGKV1-117*01 F for the V allele or the Musmus IGKJ1*01 F for the J allele, or both. The locations of the CDR regions as placed into the above backgrounds are found within the sequences of SEQ ID NOs: 42-47.

In aspects where an antibody includes a CDR region of any one or more of SEQ ID NOs: 48-55, the sequence may also include from 1-5 amino acids in the flanking FR regions on one or both sides of the CDR region as presented in any one of SEQ ID NOs: 42-47. For example, a chimeric or otherwise humanized antibody is optionally formed with amino acids on one or both sides of the relevant CDR for the purpose of ensuring proper restriction enzyme recognition and formation of nucleotide sequences encoding the full length CDR region of interest.

It is known that mouse monoclonal antibodies are highly immunogenic, which reduces their ability to be administered to humans. This may have the unwanted side effect of negatively affecting the use of some of antibodies. For example, human anti-mouse antibody (HAMA) that develops in response to the mouse antibody administrated causes immunological reactions that are unfavorable and dangerous to patients. As such, methods have been developed in the art to reduce this antigenicity or unwanted reactions when used in humans. One such method is making a chimeric antibody wherein a variable region (v region) of the antibody is derived from mouse monoclonal antibody, and a constant region (C region) thereof is derived from a suitable human antibody. Such an antibody is fully expected to maintain its affinity for target antigen as the antigen binding region is fully maintained.

A second method of forming an antibody that is more suitable for use in non-mouse organisms or optionally with non-mouse systems is by grafting one or more of the CDRs of SEQ ID NOs: 48-53 onto the respective chain of a target system antibody thereby replacing one or more of the CDR regions. As desired, however, some amino acid sequences of framework regions (FRs) supporting the CDRs may be grafted from the variable region of a mouse antibody onto the target organism variable region in order to obtain the closest possible approximation of the original mouse antibody structure. Then, the modified reshaped variable region is ligated to the constant region of the antibody from the target organism. In the finally reshaped antibody, portions derived from non-target organism amino acid sequences are only the CDRs and optionally a small portion of the FRs. The CDRs comprise hypervariable amino acid sequences and they do not show species-specific sequences. Specific methods of forming humanized antibodies, for example, can be found in Riechmann, L. et al Nature 332: 323-327, 1988; Verhoeye, M. et al., Science 239: 1534-1536, 1998; Kettleborough, C. A. et al., Protein Engng., 4: 773-783, 1991; Maeda, H., Human Antibodies and hybridoma, 2: 124-134, 1991; Gorman, S. D. et al, Proc. Natl. Acad. Sci. USA, 88: 4181-4185, 1991; Tempest, P R., Bio/Technology, 9: 226-271, 1991; Co, M. S. et al., Proc. Natl. Acad. Sci. USA 88: 2869-2873, 1991; Cater, P. et al., Proc. Natl. Acad. Sci. USA, 89: 4285-4289, 1992; Co, M. S. et al., J. Immunol., 148: 1149-1154, 1992; and Sato, K. et al., Cancer Res., 53: 851-856, 1993, U.S. Patent Application Publication No: 2004/0044187, among others.

Antibodies as used herein can be polyclonal or monoclonal. An intact antibody, a fragment thereof (e.g., Fab or $F(ab')_2$), or an engineered variant thereof (e.g., sFv) can also be used. Such antibodies can be of any immunoglobulin class including IgG, IgM, IgE, IgA, IgD and any subclass thereof.

The antibodies provided herein can be monoclonal or polyclonal, optionally a $F(ab)'^2$ fragment lacking the Fc portion of the antibody. The antibodies can be prepared by generating B cell hybridomas, or by using laboratory animals such as mouse, humanized mouse, rat, rabbit or goat that are immunized with the peptides and/or polypeptides of this invention. The peptides and/or polypeptides optionally contain deletion, insertion and/or substitution mutations. Screening can then be carried out to identify antibodies that reduce LT activity such as the assays described in Boyer et al., *Anal. Chem.*, 2007; 79 (22):8463-8470.

Monoclonal antibodies are generated by methods well known to those skilled in the art. An illustrative method is a modified version of the method of Kearney et al., *J. Immunol.* 123:1548-1558 (1979). Briefly, animals such as mice or rabbits are inoculated with the immunogen in adjuvant, and spleen cells are harvested and mixed with a myeloma cell line. The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies that enhance LT or LTx activity. Hybridomas producing antibodies are cloned, expanded and stored frozen for future production.

Techniques for the production of single chain antibodies are known to those skilled in the art and described in U.S. Pat. No. 4,946,778 and can be used to produce single chain antibodies to the motifs described herein. Phage display technology may be used to select antibody genes having binding activities for the peptides of interest.

The antibodies are useful for enhancing LT or LTx activity. The antibody is optionally modified so that it is "humanized" by transplanting the complementarity determining regions of the hybridoma-derived antibody into a human monoclonal antibody as described by Jones et al., *Nature*, 32: 1522-525 (1986).

Polyclonal antibodies can be obtained by immunizing donors with vaccines or immunogens that induce antibodies that enhance the activities of LT or LTx, and/or have other important biologic functions, e.g., neutralizing antibodies. Serum from the selected donors is then pooled and made into immunoglobulin preparations.

An antibody that is capable of enhancing the activity of LT or LTx optionally specifically recognizes an epitope of (T/S)-$X_1$-(K/R)-(D/E)-$X_2$-$X_3$ wherein $X_1$ is any amino acid, optionally phenylalanine, alanine, or histidine. In some aspects, a peptide has a sequence (T/S)-$X_1$-(K/R)-(D/E)-$X_2$-$X_3$ where: $X_1$ is any amino acid, optionally phenylalanine, alanine, or histidine; $X_2$ is any amino acid, optionally aspartic acid or glutamic acid; and $X_3$ is any non-polar or hydrophobic amino acid, optionally isoleucine or alanine. In some aspects, an antibody that is capable of enhancing the activity of LT or LTx specifically recognizes an epitope of THQDEIYEQV (SEQ ID NO. 1).

An antibody is optionally labeled or attached to a molecule such that the antibody is distinguishable from an antibody found in nature by more than sequence. Optionally, a label is optionally, but not limited to, enzymes, fluorophores, biotin, chromophores, radioisotopes, colored particles, electrochemical, chemical-modifying or chemiluminescent moieties as are known in the art. Optionally, an antibody is biotinylated in that it is bound to one or more molecules of biotin. Optionally, an antibody is bound to a fluorophore such as a fluorescein. Illustrative examples of fluorophores include HEX, ROX, Texas Red, TAMRA, JOE, Cy3, Cy5, SYBR and VIC. Illustrative examples of radioisotopes include $^{125}$I, $^{3}$H, $^{14}$C, $^{35}$S, and $^{32}$P. In some aspects, an antibody is bound to a surface such as to an assay plate or other surface. Optionally, an antibody is bound to a polystyrene or glass plate or surface. An antibody is optionally bound to a surface via an amide bond or other suitable bond.

Figure 7:
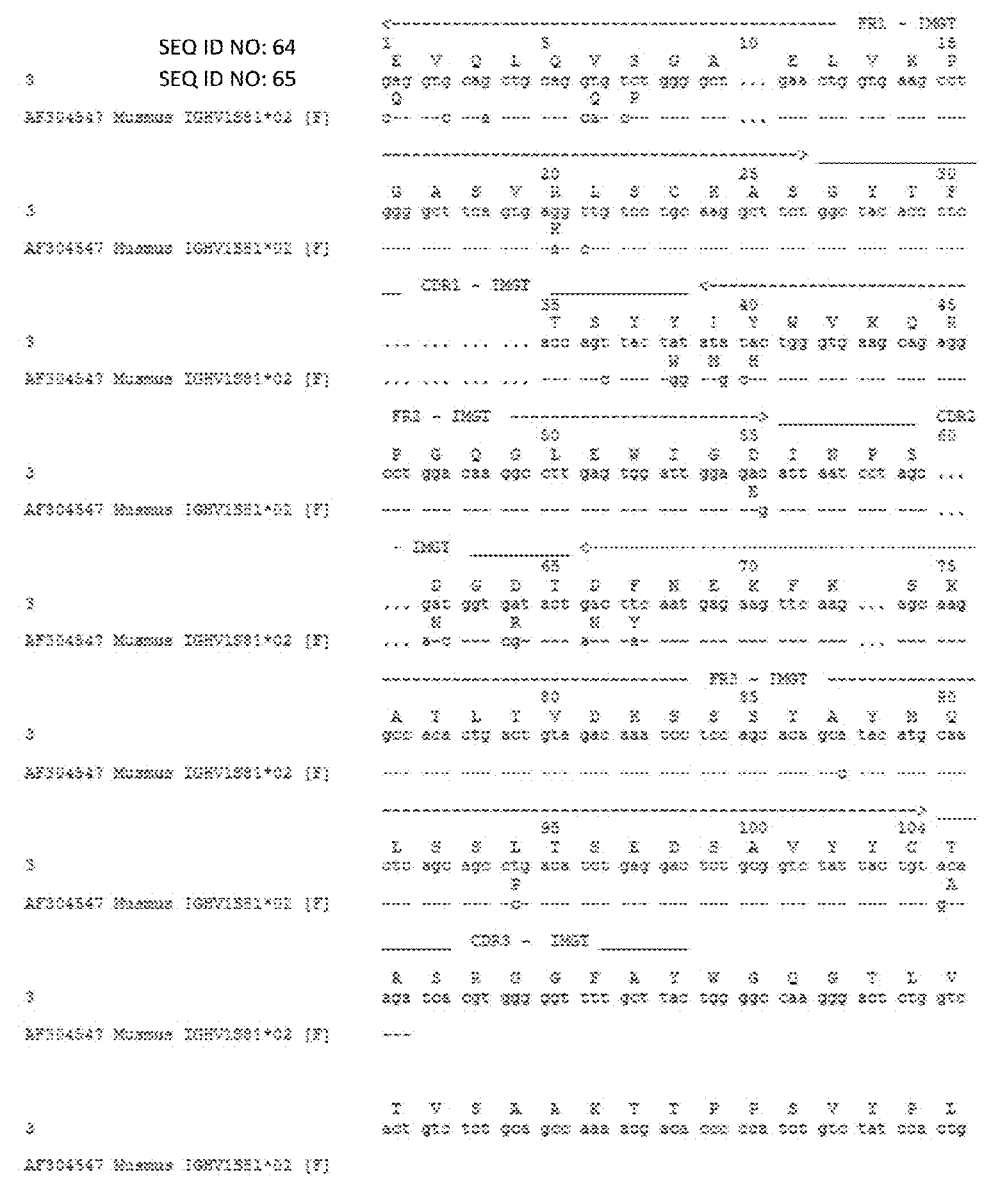

Also provided are nucleotide sequences encoding a heavy chain variable region fragment or a light chain variable region fragment of a mouse monoclonal antibody that enhances the activity of LF or LTx. A nucleotide sequence is provided that includes the nucleotide sequence encoding the heavy chain CDR1 of ggc tac acc ttc acc agt tac tat (SEQ ID NO: 56). A nucleotide sequence is provided that includes the nucleotide sequence encoding the heavy chain CDR2 of att aat cct agc gat ggt gat act (SEQ ID NO: 57). A nucleotide sequence is provided that includes the nucleotide sequence encoding the heavy chain CDR3 aca aga tca cgt ggg ggt ttt gct tac (SEQ ID NO: 58). The nucleotide sequence including the heavy chain CDR1-3 along with exemplary FR region sequences are provided in FIG. 7.

Figure 8:
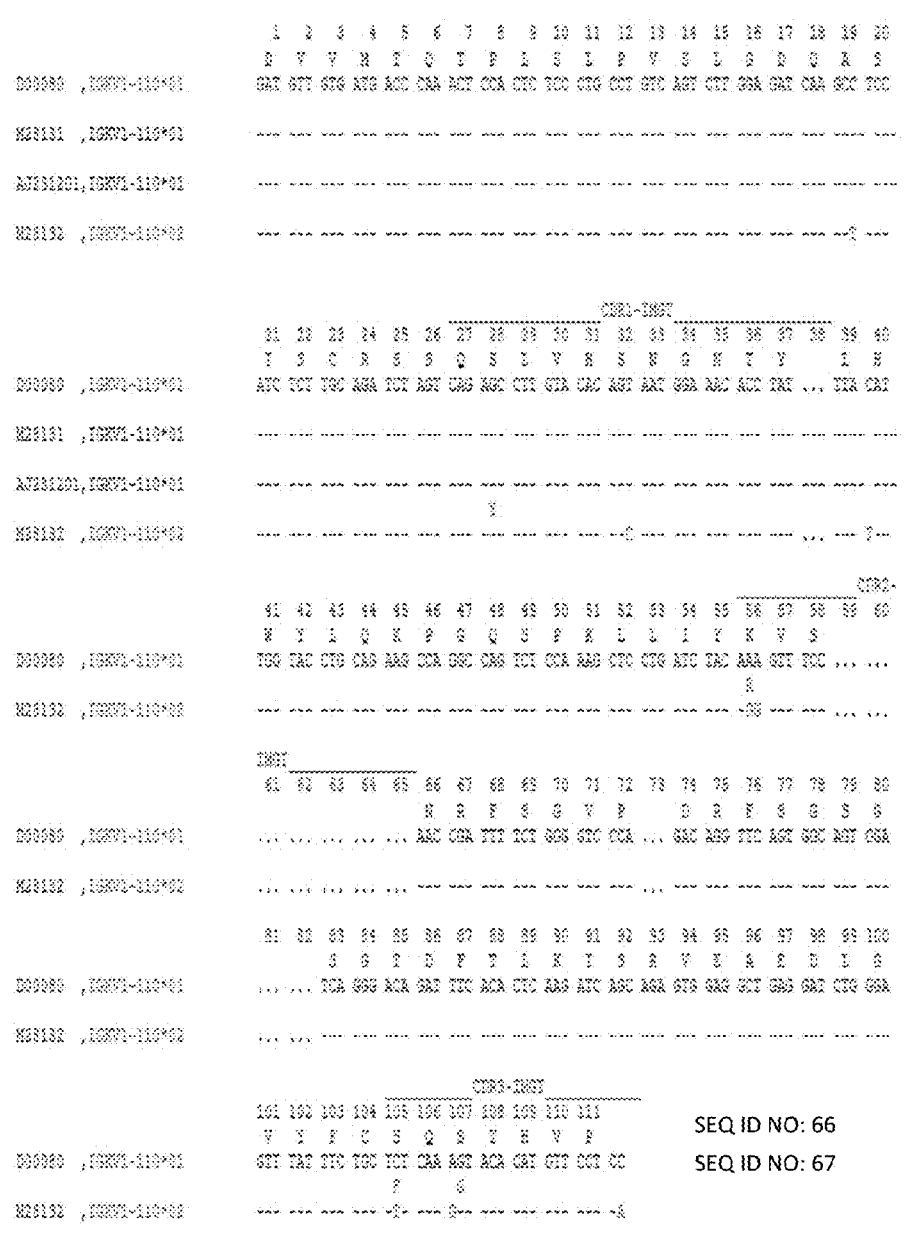

A nucleotide sequence is provided that includes the nucleotide sequence encoding the light chain CDR1 cag agc ctt gta cac agt aat gga aac acc tat (SEQ ID NO: 59). A nucleotide sequence is provided that includes the nucleotide sequence encoding the light chain CDR2 aaa gtt tcc (SEQ ID NO: 60). A nucleotide sequence is provided that includes the nucleotide sequence encoding the light chain CDR3 tct caa agt aca cat gtt cct (SEQ ID NO: 61). The nucleotide sequence including the light chain CDR1-3 along with exemplary FR region sequences are provided in FIG. 8.

Also provided are processes of enhancing LF activity, LTx activity, or both either in vitro or in vivo. A process includes combining for an activation time *B. anthracis* lethal factor with an antibody specifically recognizing a sequence (T/S)-$X_1$-(K/R)-(D/E)-$X_2$-$X_3$, the combining in an aqueous medium. Best results are achieved when an antibody and LF or LTx are combined for an activation time prior to the addition or otherwise contacting to a substrate for the LF or LTx. An activation time is optional 1 min or more. An activation time is optionally 1, 2, 3, 4, 5, 10, 15, 20, 25, 30, 60, or more minutes. An activation time is optionally 1, 1.5, 2, 2.5, 3, 4, 5, 6, 7, 8, 9, 10, 11, 12, 13, 14, 15, 20, or 24 hours. An activation time is optionally from 1 minute to 24 hours or any value or range therebetween, optionally from 1 minute to 15 hours, optionally from 1 minute to 5 hours, optionally from 1 hour to 15 hours.

An antibody is optionally bound to LF or LTx at a ratio at or greater than 1:1 antibody to LF or LTx. A ratio of antibody to LF or LTx is optionally 2:1, 3:1, 4:1, 5:1, 10:1, 20:1, 50:1, 100:1, 400:1, 500:1 or greater. A ratio of antibody to LF or LTx is optionally 1:1 to 500:1, optionally 4:1 to 500:1, optionally 400:1 to 500:1.

An antibody or process of using the antibody enhances the activity of LF or LTx relative to the LF or LTx absent the bound antibody. As used herein the word "enhances" with respect to enhancement of LF or LTx activity by an antibody means an increase in enzyme activity relative to a standard or non-antibody bound LF or LTx for a substrate. In some aspects, an antibody enhances that LF or LTx activity by a factor of 1.2, 1.4, 1.6, 1.8, 2.0, 2.5, 5, 7.5, 10 or more. Enhanced activity is optionally measured following an activation time of 2 hours, 5 hours, or 16 hours.

An immunogen of the present invention may also optionally be modified to increase its immunogenicity. In a non-limiting example, the immunogen (antigen) may be coupled to chemical compounds or immunogenic carriers, provided that the coupling does not interfere with the desired biological activity of either the antigen or the carrier. For a review of some general considerations in coupling strategies, see Antibodies, A Laboratory Manual, Cold Spring Harbor Laboratory, ed. E. Harlow and D. Lane (1988). Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads; activated carbon; or bentonite. Useful chemical compounds for coupling include, without limitation, dinitrophenol groups and arsonilic acid.

The immunogen may also be modified by other techniques illustratively including denaturation with heat and/or SDS.

An immunogen may also be used in the form of a pharmaceutically acceptable salt. Suitable acids and bases which are capable of forming salts with the polypeptides of the present invention are well known to those of skill in the art, and include inorganic and organic acids and bases.

In another aspect, the invention provides a therapeutic composition and methods for treating humans and/or animals with anthrax infection. The therapeutic composition contains an immunogen or a peptide of the sequence (T/S)-$X_1$-(K/R)-(D/E)-$X_2$-$X_3$ or (T/S)-$X_1$-(K/R)-(D/E), nucleic acid sequence encoding a peptide of (T/S)-$X_1$-(K/R)-(D/E)-$X_2$-$X_3$ or (T/S)-$X_1$-(K/R)-(D/E), or variant thereof as described herein and a suitable pharmaceutical carrier. Suitable pharmaceutically acceptable carriers facilitate administration of the peptide but are physiologically inert and/or nonharmful.

Carriers may be selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, the peptide may be combined with conventional pharmaceutical ingredients, such as preservatives, or chemical stabilizers. Suitable ingredients operable herein include, for example, casamino acids, sucrose, gelatin, phenol red, N—Z amine, monopotassium diphosphate, lactose, lactalbumin hydrolysate, and dried milk.

Alternatively, or in addition other agents useful in treating anthrax infection may be combined with a peptide, e.g., antibiotics or immunostimulatory agents and cytokine regulation elements, are expected to be useful in reducing or eliminating disease symptoms. Such agents may operate in concert with the therapeutic compositions of this invention. The development of therapeutic compositions containing these agents is within the skill of one in the art in view of the teachings of this invention.

A method of treating or preventing a *Bacillus anthracis* infection in a subject is provided including administering to the subject an effective amount of peptide, or peptide-encoding nucleic acid of this invention and optionally an anti-viral composition. The anti-viral compositions optionally include small drug-like molecule inhibitors of *Bacillus anthracis* replication and infection: nucleoside analogs such as ribavarin; EICAR; Pyrazogrin; 3-deazaguanine; GR92938X; and LY253963. These inhibitors are targeted to inhibit inosine monophosphates dehydrogenase (IMPDH). Inhibitors targeted to inhibit virus adsorption and entry are also useful. Prominent among this class are polyoxometalates and CL387626 (Wyeth-Ayerst, Pearl River, N.Y.). Other examples of polyoxometalates are T118, Trimeris' benzathrone, BABIM and RD30028.

The peptides are optionally incorporated into a pharmaceutical carrier such as saline, dextrose, water, glycerol, ethanol, other therapeutic compounds, or combinations thereof. The formulation is appropriate for the desired mode of administration and may include other immune modifiers such as heparin. The composition may also contain other additional biologically inert ingredients such as flavorants, fillers, etc.

Suitable methods of administration include, but are not limited to, intramuscular, intravenous, intranasal, mucosal, via aerosol delivery or by any route that will result in contact of a peptide with an antibody. Other non-limiting examples of such routes of administration include oral, parenteral and transdermal.

In addition, the peptides can be used to screen antisera from hyperimmune patients from whom antibodies having a very high affinity for the peptides can be derived.

Proteins, peptides or polypeptides of this invention contain the sequence of (T/S)-$X_1$-(K/R)-(D/E)-$X_2$-$X_3$ or (T/S)-$X_1$-(K/R)-(D/E), other sequences disclosed herein, variants thereof, or fragments thereof. It is appreciated that a peptide optionally includes additional amino acids N-terminal, C-terminal, or both to the sequence of (T/S)-$X_1$-(K/R)-(D/E)-$X_2$-$X_3$ or (T/S)-$X_1$-(K/R)-(D/E).

An effective amount of the compositions of this invention ranges from nanograms/kg to milligram/kg amounts for young children and adults. Based on this range, equivalent dosages for lighter or heavier body weights can be determined. The dose should be adjusted to suit the individual to whom the composition is administered and will vary with age, weight and metabolism of the individual. The exact amount of the composition required will vary from subject to subject, depending on the species, age, weight and general condition of the subject, the particular peptide or polypeptide used, its mode of administration and the like. An appropriate amount can be determined by one of ordinary skill in the art using only routine experimentation given the teachings herein. One skilled in the art will realize that dosages are best optimized by the practicing physician and methods for determining dose amounts and regimens and preparing dosage forms are described, for example, in Remington's Pharmaceutical Sciences, (Martin, E. W., ed., latest edition), Mack Publishing Co., Easton, Pa.

According to the method of the invention, a human or other animal may be treated for anthrax infection by administering an effective amount of a peptide. A more specific example of an "effective amount" is optionally between about 0.05 to about 100 µg/kg of a peptide with proper dosage easily selectable by one of skill in the art. A suitable dosage may be about 1.0 mL of such an effective amount. When given parenterally, peptide compositions are generally injected in doses ranging from 1 µg/kg to 100 mg/kg per day, optionally at doses ranging from 0.1 mg/kg to 20 mg/kg per day. The treatment may continue by continuous infusion or intermittent injection or infusion, at the same, reduced or increased dose per day for, e.g., 1 to 3 days, and additionally as determined by the treating physician.

Such a composition may be administered 1-3 times per day over a 1 day to 12 week period. However, suitable dosage adjustments may be made by the attending physician or veterinarian depending upon the age, sex, weight and general health of the subject. Such a composition is optionally administered parenterally, optionally intramuscularly or subcutaneously. However, it may also be formulated to be administered by any other suitable route, including orally or topically.

A peptide is optionally administered associated with a delivery molecule. An illustrative example of a delivery molecule is a cell penetrating peptide (CPP) such as Tat peptide or other peptide known in the art. Such CPPs are illustratively reviewed by Sebbage V, *Bioscience Horizons* (2009) 2 (1): 64-72. Optionally, a delivery molecule is an antibody that can be used to specifically target and promote cell penetration of a therapeutic peptide. Optionally, a delivery molecule is a nucleic acid, or other molecule known to improve cell permeability of a therapeutic peptide. The administration of a peptide is optionally accomplished as a pharmaceutical composition including a peptide and a pharmaceutically acceptable diluent, adjuvant, or carrier. The peptide may be administered without or in conjunction with known surfactants or other therapeutic agents. A stable pharmaceutical composition containing a peptide optionally includes the peptide at a suitable concentration in citrate buffered saline (5 or 20 mM citrate, 150 mM NaCl, pH 5.0)

comprising 0.1% by weight of poloxamer 188 (PLURONIC F-68, BASF Wyandotte, Parsippany, N.J.) and 0.002% by weight of polysorbate 80 (TWEEN 80, ICI Americas Inc., Wilmington, Del.). Another stable pharmaceutical composition containing a peptide includes the peptide at a desired concentration in 5 mM citrate, 150 mM NaCl, 0.2% poloxamer 188 and 0.002% polysorbate 80. Such combinations are described in U.S. Pat. Nos. 5,488,034 and 5,696,090 and corresponding International Publication No. WO 94/17819 (PCT/US94/01239). Peptide based constructs may be formulated like other known protein products or may be formulated in saline or a physiological buffer.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents and materials illustrated herein are commonly cross reactive between mammalian species or alternative reagents with similar properties are commercially available, and a person of ordinary skill in the art readily understands where such reagents may be obtained.

EXAMPLES

Example 1: Peptide Identification

Elucidation of the epitope for antibody AVR1674 and AVR1675 is performed by phage display analyses. The phage library includes $3\times10^9$ different peptides and is constructed in M13mp19 bacteriophage vector. The variable insert is located four amino acid residues (via linker GGGS (SEQ ID NO: 62)) from the amino terminus of protein III (pIII) and is encoded by ten NNK triplets, where N is any of the four natural DNA nucleotides (A, C, G or T) in equal mixtures and K is G or T in equal mixtures. Each NNK is thereby a mixture of 32 triplets that code for all 20 natural amino acids and one stop codon. The library ($2.0\times10^{11}$ phage particles/ml) is selected using high binding 96-well microplate Cova-link, Nunc) coated overnight with target antibody AVR1674 (from hybridoma clone LFG2:4B10) in 100 mM bicarbonate buffer (pH 9.1). The hybridoma clone referred to as LFG2:4B10 has the A.T.C.C. designation number PTA-123504, having been deposited on Oct. 18, 2016. In the first round, 100 pmol target mAb is blocked with TBST/5% BSA for 1 hr/4° C. and washed 3-times with TBST. Target is panned against phage in 150 µl of TBST (50 mM Tris-HCl, 150 mM NaCl, 0.5% TWEEN 20 (v/v), pH 7.5) at room temperature on a plate shaker for 1 h. Each sample is washed 7-times with 150 µl of TBST to eliminate non-specifically bound phage clones. Bound phages are eluted with 90 µl of 0.1 M Glycine/HCl (pH 2.2)/5% BSA for 10 min at room temperature. Eluates are neutralized with 15 µl of 2 M Tris, pH 9.1. The eluates (90 µl) are amplified by infecting 20 mL of E. coli ER2738 cells in early logarithmic phase in Luria-Bertani (LB) medium for 4-5 hrs at 37° C. on a shaker in the presence of 20 µg/ml tetracycline. E. coli cells are cooled to 4° C. and centrifuged at 12,000×g for 15 min at 4° C. Supernatants are removed and phage enriched twice by precipitation with 0.25 vols of PEG/NaCl (16.7% (w/v) polyethylene glycol 8000, 2.5 M NaCl) and alternating TBS solubilization and high-speed centrifugation to remove bacterial debris. This selection procedure is repeated two more times with amplified phage input consistently at $2.0\times10^{11}$ phage particles/ml from the preceding selection. Target mAb is reduced to 40 pmol in the second panning and 10 pmol in the third panning to increase stringency for binding. Phage is titered by standard titration and spectroscopic methods (Smith G. P. and Scott, J. K., 1993. Libraries of peptides and proteins displayed on filamentous phage. Methods Enzymol. 217, p. 228-257). For individual clone selection, E. coli cells are infected with phage from the third eluate at dilution between $1\times10^8$-10 and 10 single phage colonies (blue screen) are randomly selected. The selected clones are amplified in 20 mL of LB containing 20 µg/ml tetracycline in sterile flasks. Each clone is characterized by ELISA and ssDNA extraction.

The ability of each clone to interact with AVR1674 and 1675 is studied by ELISA. AVR1674 mAb is dissolved in carbonate buffer (150 µl/well) to the wells of a 96-well microtiter plate (Cova-link, Nunc) overnight at 4° C. Corresponding molar amounts of other antibodies are coated under the same conditions described above. The wells are washed four times with wash buffer PBST (50 mM sodium phosphate, 150 mM NaCl, 0.5% TWEEN 20 (v/v), pH 7.5) and incubated in 150 µl of blocking buffer (PBST/5% goat serum) for 1 hr at 4° C. Amplified phage particles are diluted in 150 µl/well of PBST, in triplicate, and incubated for 1 h at room temperature on a shaker. The wells are washed five times with PBST. HRP-labeled sheep anti-M13 IgG in PBST (1:5000), 150 µl per well, is added and incubated for 1 hr at room temperature. Finally, the microtiter plates are washed six times with PBST (150 µl per well), followed by the addition of 100 µl substrate. Once color development is satisfactory, 1000 of stop solution is added and mixed. Absorbance is monitored on a Spectramax 380 (Molecular Devices, Ca) plate reader at 450 nm.

Given the epitope similarity between both AVR clones, clone AVR1675/LFG2:3D10 is selected to pursue mapping. A heptapeptide library is subjected to three panning selections against pure IgG by solid-phase binding. In all selections, high affinity phage peptides are eluted by low pH briefly to improve viable phage recovery. Stringency is introduced into successive selection steps by lowering the target mAb concentration used in panning from 100 pmol to 10 pmol in the final panning selection. The input phage concentration remains constant at $2\times10^{11}$ pfu/ml each round using prior eluent. Viable phage is calculated by titrating amplified phage into competent E. coli ER2258 and counting X-gal-positive blue plaques in an agar overlay assay (Barbas, C. F. 2001. Phage display: laboratory manual. Cold Spring Laboratory Press, Cold Spring Harbor, N.Y.) To generate a consensus sequence of high confidence, Pan 3 phage clones are isolated in greater number and ELISA-positive clones were sequenced.

FIG. 1 summarizes the results of the target mAb ELISA. Typical enrichment between panning steps is observed. Clones from the third panning are isolated and tested for relative affinities to the target mAb. Sixteen clones achieve an OD≥0.5 (an arbitrary value defining high-affinity interaction) and show a 12-16-fold increase in signal from the un-enriched Pan 1. None of the clones react with mouse IgG or rabbit IgG above background eliminating non-specific protein interaction.

Successful clones are subjected to DNA sequencing analyses. Single-stranded DNA from individual phage clones is purified by NaI and ethanol precipitation. The DNA from the selected clones is amplified using the polymerase chain reaction (PCR), with the PCR protocol and necessary reagents provided with the Dye Terminator Cycle Sequencing Core Kit (PE Applied Biosystems, Foster City, Calif., USA). The primers used for the sequencing had the following nucleotide sequences: 5'-HO-GTA TGG GAT TTT GCT AAA CAA C-3' (−28 gIII primer) (SEQ ID NO: 5) and 5'-HO-CCC TCA TAG TTA GCG TAA CG-3' (−96 gIII primer) (SEQ ID NO: 6). The sequences are analyzed on an ABI Prism 377 DNA sequencer (Perkin Elmer, Foster City, Calif., USA).

DNA sequencing of all randomly selected individual clones from Pan 3 yields unambiguous sequences that permit read-through and translation of residues in the peptide insert and into pIII-fusion protein of M13 phage. The amino acid sequences are aligned by CLUSTAL-X in and are illustrated in Table 1.

TABLE 1

| Peptide | Sequence | SEQ ID NO: |
|---|---|---|
| 5c12-C5 | YAILEDH | 7 |
| AVR1674-C1 | NHHYSHL | 8 |
| AVR1674-C3 | LPLTPLP | 9 |
| AVR1674-C4 | SPEARHP | 10 |
| LF | THQDEIY | 11 |
| AVR1674-C8 | TFKDEIV | 12 |
| AVR1674-D12 | TFKDEIV | 12 |
| AVR1674-E4 | TFKDEIV | 12 |
| AVR1674-E11 | TFKDEIV | 12 |
| AVR1674-C9 | TFKDDIH | 13 |
| AVR1674-B5 | TYKDDIR | 14 |
| AVR1674-D2 | TYKDDIR | 14 |
| AVR1674-C7 | TFKDDLF | 15 |
| AVR1674-D4 | TFKDDGY | 16 |
| AVR1674-B6 | TYLDDLY | 17 |
| AVR1674-D11 | TYLDDLY | 17 |
| AVR1674-E2 | TFLDDAP | 18 |
| AVR1674-D8 | TWRDDIP | 19 |
| AVR1674-E5 | TYRDDPP | 20 |
| AVR1674-C2 | TVLDDVA | 21 |
| AVR1674-D7 | TVRDDQI | 22 |
| AVR1674-B9 | TFRDEPM | 23 |
| AVR1674-E12 | TVRDEPL | 24 |

Four high affinity peptides (AVR1674-C8, -D12, -E4 and E11) share the identical sequence TFKDEIV (SEQ ID NO: 12). This includes clone (C8). Two additional phage clones with high affinities, clones AVR1674-B5 and -D2, share sequence TYKDDIR (SEQ ID NO: 14). The remaining clones with high affinities have identical or similar amino acids at conserved positions. In general, peptides are enriched with charged and polar amino acids (Thr, Lys, Arg, Asp, Glu) and aromatic/hydrophobic residues in the second and seventh positions. Two clones with significant reduction in binding to target mAb (AVR-C2 and -D4) have unique amino acid changes in critical positions. The substitution of Leu for a basic charge in p3 reduces ELISA signal by 80% while substituting a Gly for larger hydrophobic residues eliminates binding. Control (5C12-C5) and non-binding clones have poor alignment with 16 high affinity clones. The alignment generates a 6-residue consensus sequence identified as T x K/R D D/E y x/y (x=aromatic, y=non-polar, n=no preference). The LF primary sequence is aligned against this peptide and the sequence THQDEIY (SEQ ID NO: 11) (aa 677-682 of immature LF) is identified as best match. This sequence resides in a large ordered loop (L2) found in Domain IV of LF which is inserted between two β-sheet strands, 4β2 and 4β3, where it partly obscures the active site (Pannifer A D, Wong T Y, Schwarzenbacher R, Renatus M, Petosa C, Bienkowska J, Lacy D B, Collier R J, Park S, Leppla S H, Hanna P, Liddington R C. 2001. Crystal structure of the anthrax lethal factor. Nature. 2001 Nov. 8; 414(6860):229-33.). Upon closer examination of the LF solvent-exposed L2 (1J7N; RasMol) the most conserved residues of the putative epitope (Thr677, Asp680, Glu681) extends outward from the strands while the surrounding residues are oriented toward the interior of the molecule. These residues are thus coordinated in an exposed plane amenable to contact with CDR residues of the target antibody.

Example 2: Peptide Characterization

To further elucidate the core required peptide sequences necessary for binding AVR1674 and preventing its interaction with LF, synthetic peptides are designed against the predicted epitope in LF and reference phage clone AVR1674-C8. Testing the isolated peptide removes possibility of mAb binding via non-specific phage proteins. Additionally both phage and LF sequences can be measured accurately for relative and kinetic binding to target mAb. Peptide sequences are modifications of AVR1674-C8 and are listed in Table 2:

TABLE 2

| Peptide | SEQ ID NO: |
|---|---|
| TFKDEIGGGSK-biotin | 25 |
| AFKDEIGGGSK-biotin | 26 |
| TAKDEIGGGSK-biotin | 27 |
| TFADEIGGGSK-biotin | 28 |
| TFKAEIGGGSK-biotin | 29 |
| TFKDAIGGGSK-biotin | 30 |
| TEKDEAGGGSK-biotin | 31 |
| AFKDEIGGGSK-biotin | 32 |
| TAKDEIGGGSK-biotin | 33 |
| TFADEIGGGSK-biotin | 34 |
| TFKAEIGGGSK-biotin | 35 |
| THKDEIGGGSK-biotin | 36 |
| TEQDEIGGGSK-biotin | 37 |
| THQDEIYEQK-biotin | 38 |

In addition to phage peptide (AVR1674-C8 TFKDEIGGGSK-bio) (SEQ ID NO: 25) two peptides are designed to provide a putative epitope of LF (THQDEIYEQK-bio) (SEQ ID NO: 38) and an extended LF peptide (mature LF$_{637-664}$ bio-PNIAEQYTHQDEIYEQVHSKGLYVPESR) (SEQ ID NO: 39), which has the entire L2 and 4β3 sequences to introduce possible structural elements. The ability of the peptides to bind to mAb AVR1674 is studied by competitive ELISA or biolayer interferometry.

Figure 2:
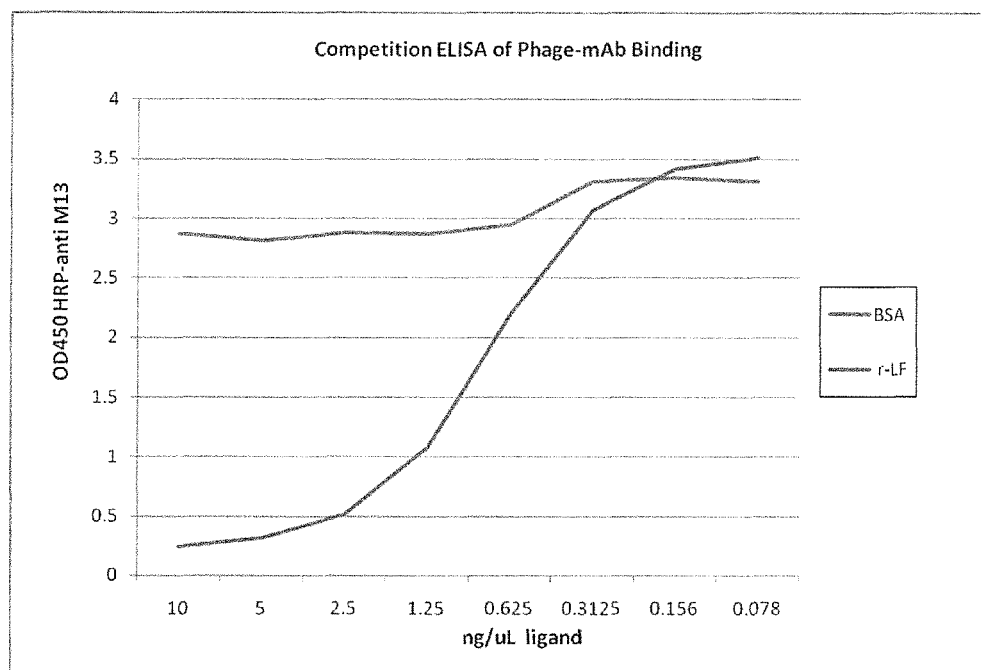
FIG. 2 illustrates inhibition of antibody binding to LF by the phage displaying peptide AVR-1674 CS.

Each of the peptides of Table 2 is subjected to a competition assay using recombinant LF as the competing ligand. Recombinant LF at 0-10 μg/ml is pre-incubated with phage clones or isolated peptides (with or without biotinylation) for 10 min at room temperature. Phage and r-LF are diluted in 150 μl/well of PBST, in triplicate, and incubated for 1 h at room temperature on 96-well plate coated with 15 ug/ml mAb. The wells are washed five times with PBST. HRP-labeled sheep anti-M13 IgG in PBST (1:5000), 150 μl per well, is added and incubated for 1 hr at room temperature. ELISA is developed as discussed in Example 1. The inhibition of binding by the phage displaying peptide of AVR- 1674 C8 is illustrated in FIG. 2. These results demonstrate that phage binds competitively with r-LF for the antibody binding domain. BSA has no effect in phage-mAb interaction.

For biolayer interferometry, isolated biotinylated peptides of Table 2 are synthesized. Octet Qke analysis is performed at temperature control at 30° C. in PBS buffer. Streptavidin (SA) sensors are pre-wet for 10 min in buffer prior to use and microplates used in the Octet are filled with 200 μl of sample or buffer and agitated at 700 rpm. SA-coated tips are saturated with 25 μg/ml biotinylated synthetic peptides. Typical capture levels are 0.70±0.15 nm within a row of eight tips with the standard deviation within the instrument noise. A nM titration of LFG2:4B10 mAb is bound for 500 s and allowed to dissociate for 500 s in PBS buffer. Dissociation buffer was used only once to prevent non-specific binding. Blank binding cycles containing only peptide are used to correct for baseline drift. Peptides are compared in the same experiment by coupling each onto its own tips in triplicate. Shift data from the Octet are exported for processing and analysis in Data Analysis 6.4. To deduce a direct binding affinity via the kinetic rate constants ($_{KD}=_{koff}/_{kon}$, where KD=equilibrium dissociation rate constant, $_{kon}$=association rate constant, and $_{koff}$=dissociation rate constant) the buffer subtracted Octet data are fit globally to a simple 1:1 Langmuir model.

A significant improvement in binding response by nearly 7-fold (4.83 nm vs. 0.7 nm) and dissociation (13.9 nM vs. 53 nM) is exhibited using the phage peptide AVR 1674-C8 (TFKDEIGGGSK-biotin; SEQ ID NO: 25) rather than native epitope (THQDEIYEQK-biotin; SEQ ID NO: 38) (Table 3). The putative LF sequence is sufficient for binding the target mAb with no effect of sequence outside the THQDEIYEQ (SEQ ID NO: 40) epitope containing sequence in the L2. Furthermore, the discovered sequence (TFKDEI; SEQ ID NO: 4) in phage enhances binding through molecular interactions not present in the synthetic peptide structure and/or primary sequence. To obtain a more accurate kinetic determination of the phage peptide below saturation conditions, a titration of mAb LFG2 is tested against peptide in a follow-up experiment. A higher affinity ($K_D$=9.97 nM) is calculated with a 4-point titration curve. This approximates dissociation constants ($K_D$=≤10 nM) for anti-LF mAbs previously studied (data not shown). Similar studies are performed on all peptides of Table 2. The results are illustrated in Table 3.

TABLE 3

| Peptide | SEQ ID NO: | Assoc. (Sample) Loc. | Conc. (nM) | Response R | $K_D$ (M) |
|---|---|---|---|---|---|
| TFKDEIGGGSK-biotin | 25 | A4 | 500 | 4.8387 | 1.39E-08 |
| AFKDEIGGGSK-biotin | 26 | 84 | 500 | 0.5352 | 3.51E-08 |
| TAKDEIGGGSK-biotin | 27 | C4 | 500 | 3.7854 | 3.15E-08 |
| TFADEIGGGSK-biotin | 28 | D4 | 500 | 0.4475 | 2.52E-08 |
| TFKAEIGGGSK-biotin | 29 | E4 | 500 | 0.2612 | na |
| TFKDAIGGGSK-biotin | 30 | F4 | 500 | 1.0132 | 2.45E-08 |
| TFKDEAGGGSK-biotin | 31 | G4 | 500 | 5.2909 | 1.64E-08 |
| AFKDEIGGGSK-biotin | 32 | B4 | 500 | 0.556 | 2.87E-08 |
| TAKDEIGGGSK-biotin | 33 | C4 | 500 | 3.7743 | 2.09E-08 |
| TFADEIGGGSK-biotin | 34 | D4 | 500 | 0.4596 | 2.39E-08 |
| TFKAEIGGGSK-biotin | 35 | E4 | 500 | 0.2492 | n/a |
| THKDEIGGGSK-biotin | 36 | F4 | 500 | 2.3704 | 0.00000006 |
| TFQDEIGGGSK-biotin | 37 | G4 | 500 | 1.3414 | 3.44E-08 |
| THQDEIYEQK-biotin | 38 | H4 | 500 | 0.7024 | 5.31E-08 |

Example 3: Inhibition of the Stimulation of LT Activity

The activity of LF is assayed in 40 μL total volume of reaction buffer (RB) containing 20 mM HEPES buffer pH 7.3, 1 mM DTT, 20 μM $CaCl_2$, 10 mM $MgCl_2$, 20 μM ZnCl2, protease inhibitor mix, and 2 nmol of substrate peptide LF-4 described in Boyer et al., *Anal. Chem.,* 2007; 79 (22):8463-8470.

Figure 3A:
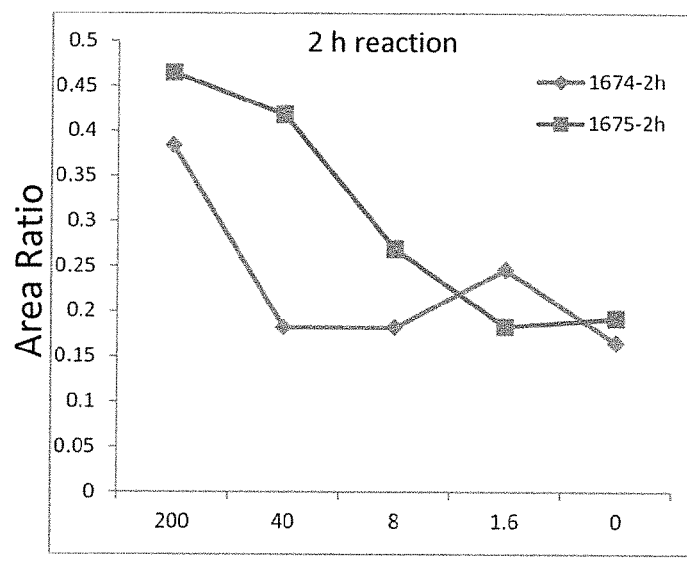
FIG. 3A illustrates enhancement of LF activity by antibodies AVR1674 and AVR1675 at 2 hours of incubation.
Figure 3B:
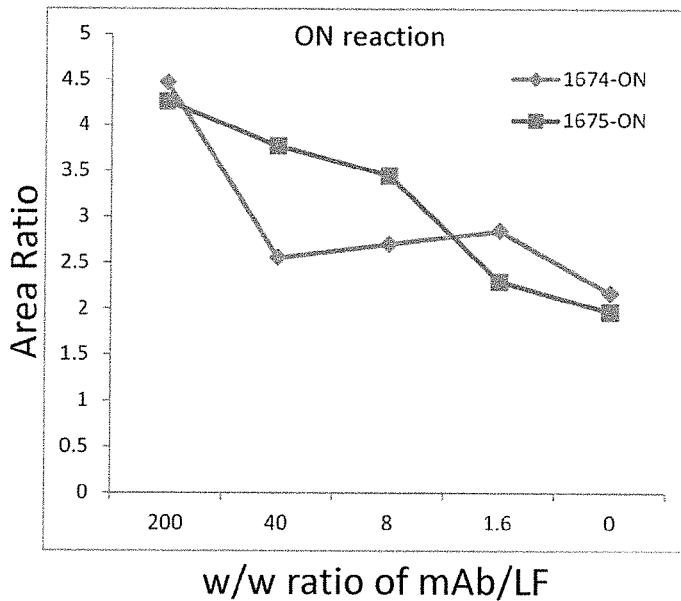
FIG. 3B illustrates enhancement of LF activity by antibodies AVR1674 and AVR1675 at 16 hours of incubation.
Figure 3C:
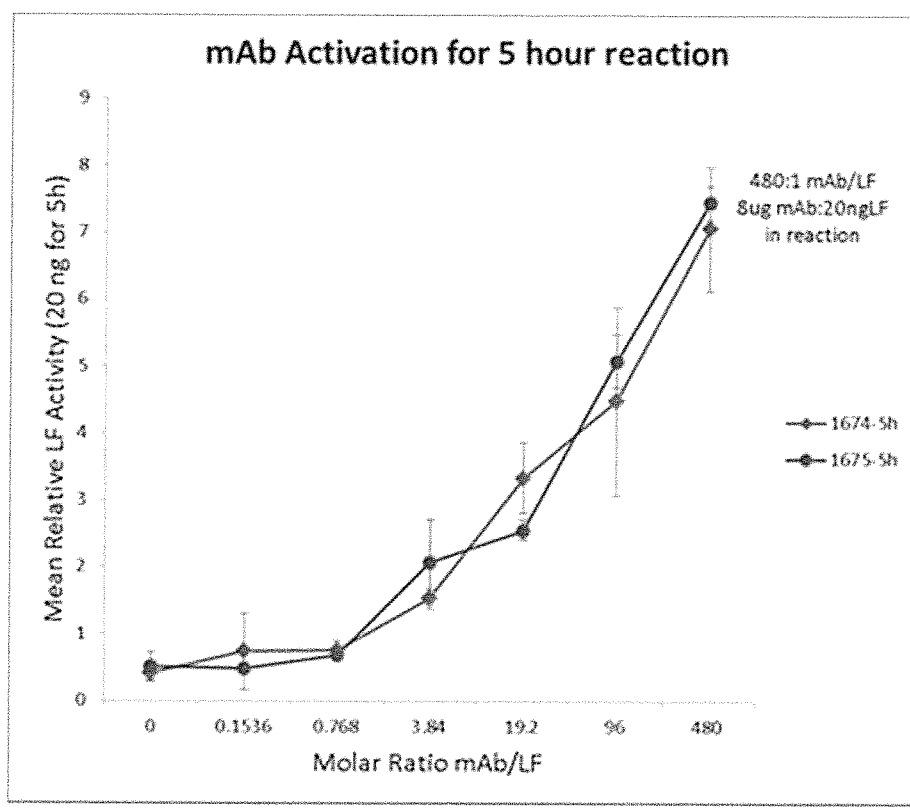
FIG. 3C illustrates enhancement of LF activity by antibodies AVR1674 and AVR1675 at 5 hours of incubation.
Figure 9:
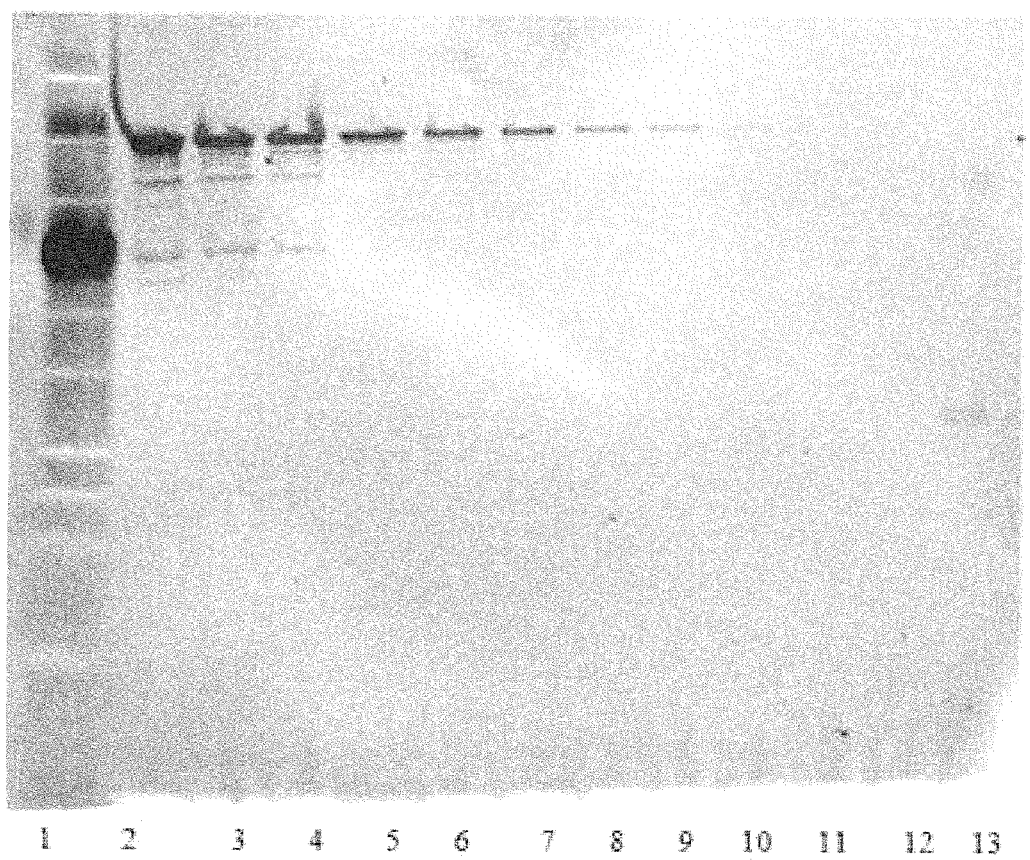
FIG. 9 illustrates an immunoblot of an exemplary antibody AVR 1674 (200 µg/ml) illustrating specificity for a linear epitope in denatured recombinant lethal factor with lane 1 ladder, lanes 2-10 of 2 µg, 1 µg, 500 ng, 250 ng, 125 ng, 62 ng, 31 ng, 15 ng, 7 ng, respectively, lane 11 of recombinant protective antigen at 500 ng, lane 12 of bovine serum albumin at 500 ng, and lane 13 of AVR 1674 LFG2-4B1- at 125 ng.
Figure 4A:
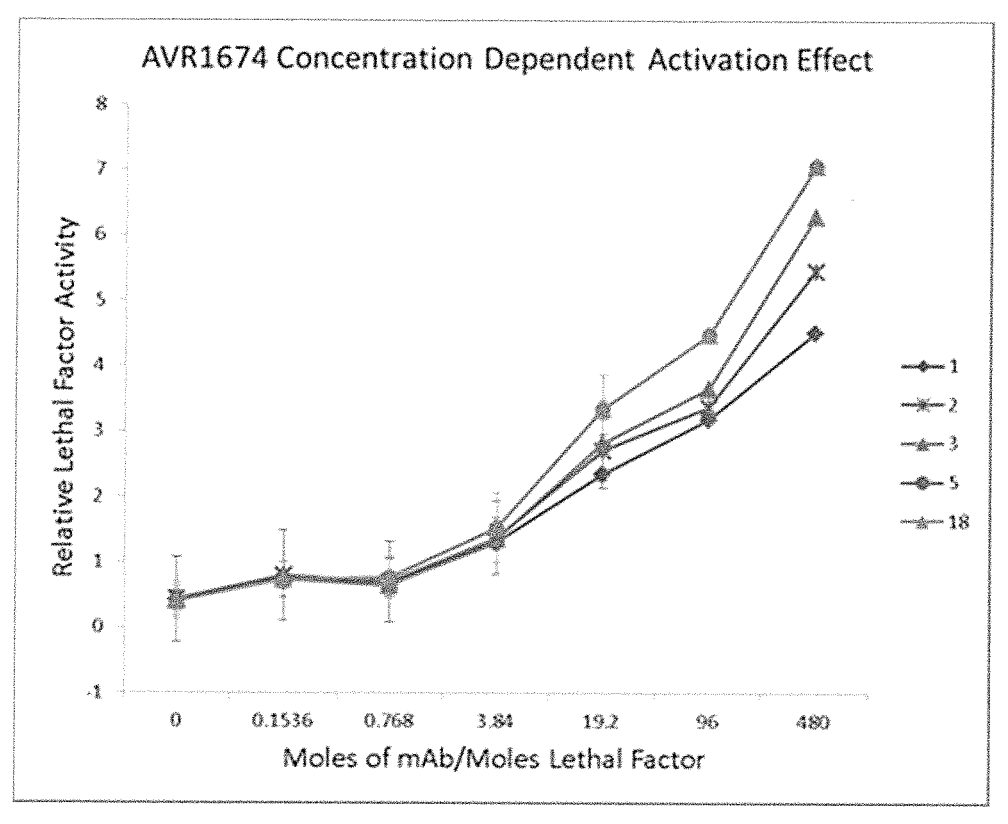
Figure 4B:
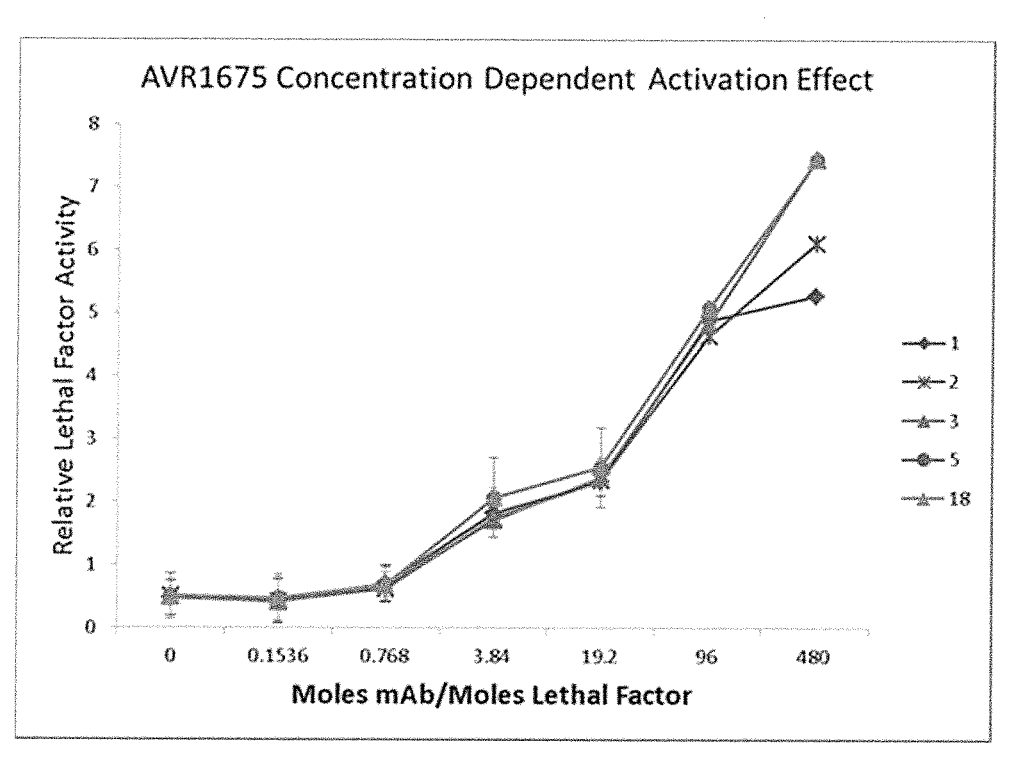

When assayed alone, both antibody AVR1674 and AVR1675 enhance the activity of LF. (FIG. 3) FIG. 3A illustrates a 2 hour incubation of antibody with LF prior to substrate cleavage. FIG. 3B illustrates a 16 hour incubation. FIG. 3C illustrates onset time of enhancement of LF activity with AVR1674 or AVR1675 following a 5 hour reaction demonstrating that the sequence of (T/S)-$X_1$-(K/R)-(D/E)-$X_2$-$X_3$ or (T/S)-$X_1$-(K/R)-(D/E) is essential for enhancing antibody induced activity. With increasing antibody to LF ratio, greater activity is observed. FIG. 4A illustrates a concentration dependent activation of LF by antibody AVR1674. FIG. 4B illustrates a concentration dependent activation of LF by antibody AVR1675.

For MALDI-TOF MS detection, a 1- or 2-4 aliquot of the LF reaction mixture is removed and added respectively to 9 or 18 μL of α-cyano-4-hydroxycinnamic acid (CHCA) at 5 mg/mL in 50% acetonitrile, 0.1% trifluoroacetic acid, and 1 mM ammonium phosphate (CHCA matrix), with or without 1 pmol of NT- and optionally CT-ISTD, mixed, and 0.5 µL is spotted in triplicate onto a 192-spot stainless steel MALDI plate (Applied Biosystems, Framingham, Mass.), and then mass spectra are collected from 750 to 3200 mass/charge (m/z) or as described, in MS positive ion reflectron mode on the Applied Biosystems 4700 Proteomics Analyzers (Framingham, Mass.). This instrument uses a nitrogen laser at 337 nm, and each final mass spectrum is an average of spectra obtained from 2400 laser shots.

LF in a sample is incubated with RB, antibody AVR1674, AVR1675, or both, and substrate in the presence or absence of each of the peptides of Table 2 at 37° C. for 2 h, and a 1-µL aliquot of the reaction is used for MALDI-TOF MS analysis. Each of the peptides of Table 2 reduces the activity of LF enhanced by antibody AVR1674.

Example 3: Production of Antibodies

LFG2-4B10 mAb IgG1/AVR1674 (LFG2 3F3:3H9:2C10:4B10) and AVR1675 mAb (LFG2 3F3:3H9:2C10:3D10) hybridomas were obtained from SP2/0 fused B-cells from a LF-immunized balb/c mouse. Three successive rounds of limiting dilution cloning recovered these clones upon screening against r-LF and purified from hybridoma culture by HITRAP Protein G sepharose affinity chromatography (GE Biosciences, Piscataway, N.J.). Protein G-purified IgG1 kappa mAb was concentrated to 5 mg/ml in 50 mM HEPES/150 mM NaCl (pH 7.4) and frozen at −40° C. The protein was analyzed by SDS-PAGE and Superdex-200 size-exclusion chromatography to assess purity and degradation/aggregation. The mAb was able to detect below 30 ng of LF by immunoblot (FIG. 9) indicating affinity to a continuous epitope in the denatured antigen.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents and publications mentioned in the specification are indicative of the levels of those skilled in the art to which the invention pertains. These patents and publications are incorporated herein by reference to the same extent as if each individual application or publication was specifically and individually stated herein as incorporated herein by reference for the entirety of their teaching.

The foregoing description is illustrative of particular embodiments of the invention, but is not meant to be a limitation upon the practice thereof. The following claims, including all equivalents thereof, are intended to define the scope of the invention.

We claim:

1. The monoclonal antibody AVR1674 produced by hybridoma clone LFG2:4B10 that is deposited as PTA-123504.

2. A composition comprising the monoclonal antibody of claim 1.

3. The monoclonal antibody of claim 1, wherein said antibody is labeled.

4. A hybridoma clone LFG2:4B10 that is deposited under ATCC accession number PTA-123504.

5. The monoclonal antibody of claim 1, wherein the antibody is bound to a polystyrene, glass plate, or glass surface.

* * * * *

SEQUENCE LISTING

```
<160> NUMBER OF SEQ ID NOS: 67

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Thr His Gln Asp Glu Ile Tyr Glu Gln Val
1               5                   10

<210> SEQ ID NO 2
<211> LENGTH: 833
<212> TYPE: PRT
<213> ORGANISM: Artificial Sequence
<220> FEATURE:
<223> OTHER INFORMATION: Wild-type immature LF sequence

<400> SEQUENCE: 2

Trp Ile Leu Asp Thr Tyr Pro Glu Ile Met Met Ala Thr Arg Glu Leu
1               5                   10                  15

Phe Ser Glu Gln Glu Asn Cys Glu Met Asn Ile Lys Lys Glu Phe Ile
            20                  25                  30

Lys Val Ile Ser Met Ser Cys Leu Val Thr Ala Ile Thr Leu Ser Gly
        35                  40                  45

Pro Val Phe Ile Pro Leu Val Gln Gly Ala Gly Gly His Gly Asp Val
    50                  55                  60

Gly Met His Val Lys Glu Lys Glu Lys Asn Lys Asp Glu Asn Lys Arg
65                  70                  75                  80

Lys Asp Glu Glu Arg Asn Lys Thr Gln Glu Glu His Leu Lys Glu Ile
                85                  90                  95
```

```
Met Lys His Ile Val Lys Ile Glu Val Lys Gly Glu Glu Ala Val Lys
                100                 105                 110
Lys Glu Ala Ala Glu Lys Leu Leu Glu Lys Val Pro Ser Asp Val Leu
            115                 120                 125
Glu Met Tyr Lys Ala Ile Gly Gly Lys Ile Tyr Ile Val Asp Gly Asp
        130                 135                 140
Ile Thr Lys His Ile Ser Leu Glu Ala Leu Ser Asp Lys Lys Lys
145                 150                 155                 160
Ile Lys Asp Ile Tyr Gly Lys Asp Ala Leu His Glu His Tyr Val
                165                 170                 175
Tyr Ala Lys Glu Gly Tyr Glu Pro Val Leu Val Ile Gln Ser Ser Glu
            180                 185                 190
Asp Tyr Val Glu Asn Thr Glu Lys Ala Leu Asn Val Tyr Tyr Glu Ile
        195                 200                 205
Gly Lys Ile Leu Ser Arg Asp Ile Leu Ser Lys Ile Asn Gln Pro Tyr
    210                 215                 220
Gln Lys Phe Leu Asp Val Leu Asn Thr Ile Lys Asn Ala Ser Asp Ser
225                 230                 235                 240
Asp Gly Gln Asp Leu Leu Phe Thr Asn Gln Leu Lys Glu His Pro Thr
                245                 250                 255
Asp Phe Ser Val Glu Phe Leu Glu Gln Asn Ser Asn Glu Val Gln Glu
            260                 265                 270
Val Phe Ala Lys Ala Phe Ala Tyr Ile Glu Pro Gln His Arg Asp
        275                 280                 285
Val Leu Gln Leu Tyr Ala Pro Glu Ala Phe Asn Tyr Met Asp Lys Phe
    290                 295                 300
Asn Glu Gln Glu Ile Asn Leu Ser Leu Glu Glu Leu Lys Asp Gln Arg
305                 310                 315                 320
Met Leu Ala Arg Tyr Glu Lys Trp Glu Lys Ile Lys Gln His Tyr Gln
                325                 330                 335
His Trp Ser Asp Ser Leu Ser Glu Glu Gly Arg Gly Leu Leu Lys Lys
            340                 345                 350
Leu Gln Ile Pro Ile Glu Pro Lys Lys Asp Asp Ile Ile His Ser Leu
        355                 360                 365
Ser Gln Glu Glu Lys Glu Leu Leu Lys Arg Ile Gln Ile Asp Ser Ser
    370                 375                 380
Asp Phe Leu Ser Thr Glu Glu Lys Glu Phe Leu Lys Lys Leu Gln Ile
385                 390                 395                 400
Asp Ile Arg Asp Ser Leu Ser Glu Glu Lys Glu Leu Leu Asn Arg
                405                 410                 415
Ile Gln Val Asp Ser Ser Asn Pro Leu Ser Glu Lys Glu Lys Glu Phe
            420                 425                 430
Leu Lys Lys Leu Lys Leu Asp Ile Gln Pro Tyr Asp Ile Asn Gln Arg
        435                 440                 445
Leu Gln Asp Thr Gly Gly Leu Ile Asp Ser Pro Ser Ile Asn Leu Asp
    450                 455                 460
Val Arg Lys Gln Tyr Lys Arg Asp Ile Gln Asn Ile Asp Ala Leu Leu
465                 470                 475                 480
His Gln Ser Ile Gly Ser Thr Leu Tyr Asn Lys Ile Tyr Leu Tyr Glu
                485                 490                 495
Asn Met Asn Ile Asn Asn Leu Thr Ala Thr Leu Gly Ala Asp Leu Val
            500                 505                 510
Asp Ser Thr Asp Asn Thr Lys Ile Asn Arg Gly Ile Phe Asn Glu Phe
```

```
                515                 520                 525
Lys Lys Asn Phe Lys Tyr Ser Ile Ser Ser Asn Tyr Met Ile Val Asp
        530                 535                 540

Ile Asn Glu Arg Pro Ala Leu Asp Asn Glu Arg Leu Lys Trp Arg Ile
545                 550                 555                 560

Gln Leu Ser Pro Asp Thr Arg Ala Gly Tyr Leu Glu Asn Gly Lys Leu
                565                 570                 575

Ile Leu Gln Arg Asn Ile Gly Leu Glu Ile Lys Asp Val Gln Ile Ile
            580                 585                 590

Lys Gln Ser Glu Lys Glu Tyr Ile Arg Ile Asp Ala Lys Val Val Pro
        595                 600                 605

Lys Ser Lys Ile Asp Thr Lys Ile Gln Glu Ala Gln Leu Asn Ile Asn
610                 615                 620

Gln Glu Trp Asn Lys Ala Leu Gly Leu Pro Lys Tyr Thr Lys Leu Ile
625                 630                 635                 640

Thr Phe Asn Val His Asn Arg Tyr Ala Ser Asn Ile Val Glu Ser Ala
                645                 650                 655

Tyr Leu Ile Leu Asn Glu Trp Lys Asn Asn Ile Gln Ser Asp Leu Ile
            660                 665                 670

Lys Lys Val Thr Asn Tyr Leu Val Asp Gly Asn Gly Arg Phe Val Phe
        675                 680                 685

Thr Asp Ile Thr Leu Pro Asn Ile Ala Glu Gln Tyr Thr His Gln Asp
        690                 695                 700

Glu Ile Tyr Glu Gln Val His Ser Lys Gly Leu Tyr Val Pro Glu Ser
705                 710                 715                 720

Arg Ser Ile Leu Leu His Gly Pro Ser Lys Gly Val Glu Leu Arg Asn
                725                 730                 735

Asp Ser Glu Gly Phe Ile His Glu Phe Gly His Ala Val Asp Asp Tyr
            740                 745                 750

Ala Gly Tyr Leu Leu Asp Lys Asn Gln Ser Asp Leu Val Thr Asn Ser
        755                 760                 765

Lys Lys Phe Ile Asp Ile Phe Lys Glu Glu Gly Ser Asn Leu Thr Ser
        770                 775                 780

Tyr Gly Arg Thr Asn Glu Ala Glu Phe Phe Ala Glu Ala Phe Arg Leu
785                 790                 795                 800

Met His Ser Thr Asp His Ala Glu Arg Leu Lys Val Gln Lys Asn Ala
                805                 810                 815

Pro Lys Thr Phe Gln Phe Ile Asn Asp Gln Ile Lys Phe Ile Ile Asn
            820                 825                 830

Ser

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Gly Gly Gly Ser Lys
1               5

<210> SEQ ID NO 4
<211> LENGTH: 6
<212> TYPE: PRT
<213> ORGANISM: Artificial Sequence
```

```
<220> FEATURE:
<223> OTHER INFORMATION: Synthetic peptide

<400> SEQUENCE: 4

Thr Phe Lys Asp Glu Ile
1               5

<210> SEQ ID NO 5
<211> LENGTH: 22
<212> TYPE: DNA
<213> ORGANISM: Bacillus anthracis

<400> SEQUENCE: 5
gtatgggatt tgctaaaca ac                                                 22

<210> SEQ ID NO 6
<211> LENGTH: 20
<212> TYPE: DNA
<213> ORGANISM: Bacillus anthracis

<400> SEQUENCE: 6
ccctcatagt tagcgtaacg                                                   20

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Tyr Ala Ile Leu Glu Asp His
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Asn His His Tyr Ser His Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Leu Pro Leu Thr Pro Leu Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ser Pro Glu Ala Arg His Pro
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Thr His Gln Asp Glu Ile Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Thr Phe Lys Asp Glu Ile Val
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Thr Phe Lys Asp Asp Ile His
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Thr Tyr Lys Asp Asp Ile Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Thr Phe Lys Asp Asp Leu Phe
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Thr Phe Lys Asp Asp Gly Tyr
1               5
```

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Thr Tyr Leu Asp Asp Leu Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Thr Phe Leu Asp Asp Ala Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Thr Trp Arg Asp Asp Ile Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Thr Tyr Arg Asp Asp Pro Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Thr Val Leu Asp Asp Val Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Thr Val Arg Asp Asp Gln Ile
1               5

```
<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Thr Phe Arg Asp Glu Pro Met
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Thr Val Arg Asp Glu Pro Leu
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Thr Phe Lys Asp Glu Ile Gly Gly Gly Ser Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Ala Phe Lys Asp Glu Ile Gly Gly Gly Ser Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Thr Ala Lys Asp Glu Ile Gly Gly Gly Ser Lys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28

Thr Phe Ala Asp Glu Ile Gly Gly Gly Ser Lys
1               5                   10

<210> SEQ ID NO 29
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Thr Phe Lys Ala Glu Ile Gly Gly Gly Ser Lys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

<400> SEQUENCE: 30

Thr Phe Lys Asp Ala Ile Gly Gly Gly Ser Lys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide

<400> SEQUENCE: 31

Thr Phe Lys Asp Glu Ala Gly Gly Gly Ser Lys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide

<400> SEQUENCE: 32

Ala Phe Lys Asp Glu Ile Gly Gly Gly Ser Lys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Thr Ala Lys Asp Glu Ile Gly Gly Gly Ser Lys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide

<400> SEQUENCE: 34

Thr Phe Ala Asp Glu Ile Gly Gly Gly Ser Lys
1               5                   10

<210> SEQ ID NO 35
<211> LENGTH: 11
```

<212> TYPE: PRT
<213> ORGANISM: Artificial Sequence
<220> FEATURE:
<223> OTHER INFORMATION: Synthetic peptide

<400> SEQUENCE: 35

Thr Phe Lys Ala Glu Ile Gly Gly Gly Ser Lys
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic peptide

<400> SEQUENCE: 36

Thr His Lys Asp Glu Ile Gly Gly Gly Ser Lys
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide

<400> SEQUENCE: 37

Thr Phe Gln Asp Glu Ile Gly Gly Gly Ser Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide

<400> SEQUENCE: 38

Thr His Gln Asp Glu Ile Tyr Glu Gln Lys
1               5                   10

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

Pro Asn Ile Ala Glu Gln Tyr Thr His Gln Asp Glu Ile Tyr Glu Gln
1               5                   10                  15

Val His Ser Lys Gly Leu Tyr Val Pro Glu Ser Arg
            20                  25

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Thr His Gln Asp Glu Ile Tyr Glu Gln
1               5

```
<210> SEQ ID NO 41
<211> LENGTH: 10
<212> TYPE: PRT
<213> ORGANISM: Artificial Sequence
<220> FEATURE:
<223> OTHER INFORMATION: Synthetic peptide

<400> SEQUENCE: 41

Thr His Gln Asp Glu Ile Phe Glu Gln Lys
1               5                   10

<210> SEQ ID NO 42
<211> LENGTH: 162
<212> TYPE: PRT
<213> ORGANISM: Artificial Sequence
<220> FEATURE:
<223> OTHER INFORMATION: Synthetic peptide

<400> SEQUENCE: 42

Glu Val Gln Leu His Glu Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
                20                  25                  30

Tyr Ile Tyr Trp Val Lys Gln Arg Pro Gly Gln Gly Leu Glu Trp Ile
            35                  40                  45

Gly Asp Ile Asn Pro Ser Asp Gly Asp Thr Asp Phe Asn Glu Lys Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Ser Arg Gly Gly Phe Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu

<210> SEQ ID NO 43
<211> LENGTH: 161
<212> TYPE: PRT
<213> ORGANISM: Artificial Sequence
<220> FEATURE:
<223> OTHER INFORMATION: Synthetic peptide

<400> SEQUENCE: 43

Glu Val Gln Leu Gln Val Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
                20                  25                  30

Tyr Ile Tyr Trp Val Lys Gln Arg Pro Gly Gln Gly Leu Glu Trp Ile
            35                  40                  45

Gly Asp Ile Asn Pro Ser Asp Gly Asp Thr Asp Phe Asn Glu Lys Phe
        50                  55                  60

Lys Ser Lys Ala Thr Leu Thr Val Asp Lys Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Thr Arg Ser Arg Gly Gly Phe Ala Tyr Trp Gly Gln Gly Thr Leu Val
            100                 105                 110

Thr Val Ser Ala Ala Lys Thr Thr Pro Pro Ser Val Tyr Pro Leu Ala
            115                 120                 125

Pro Gly Ser Ala Ala Gln Thr Asn Ser Met Val Thr Leu Gly Cys Leu
            130                 135                 140

Val Lys Gly Tyr Phe Pro Glu Pro Val Thr Val Thr Trp Asn Ser Gly
145                 150                 155                 160

Ser

<210> SEQ ID NO 44
<211> LENGTH: 160
<212> TYPE: PRT
<213> ORGANISM: Artificial Sequence
<220> FEATURE:
<223> OTHER INFORMATION: Synthetic peptide

<400> SEQUENCE: 44

Val Gln Leu Gln Glu Ser Gly Ala Glu Leu Val Lys Pro Gly Ala Ser
1               5                   10                  15

Val Arg Leu Ser Cys Lys Ala Ser Gly Tyr Thr Phe Thr Ser Tyr Tyr
                20                  25                  30

Ile Tyr Trp Val Lys Gln Arg Pro Gly Gln Gly Leu Glu Trp Ile Gly
            35                  40                  45

Asp Ile Asn Pro Ser Asp Gly Asp Thr Asp Phe Asn Glu Lys Phe Lys
50                  55                  60

Ser Lys Ala Thr Leu Thr Val Asp Lys Ser Ser Ser Thr Ala Tyr Met
65                  70                  75                  80

Gln Leu Ser Ser Leu Thr Ser Glu Asp Ser Ala Val Tyr Tyr Cys Thr
                85                  90                  95

Arg Ser Arg Gly Gly Phe Ala Tyr Trp Gly Gln Gly Thr Leu Val Thr
            100                 105                 110

Val Ser Ala Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
            130                 135                 140

Lys Gly Tyr Phe Pro Glu Pro Val Thr Val Thr Trp Asn Ser Gly Ser
145                 150                 155                 160

<210> SEQ ID NO 45
<211> LENGTH: 83
<212> TYPE: PRT
<213> ORGANISM: Artificial Sequence
<220> FEATURE:
<223> OTHER INFORMATION: Synthetic peptide

<400> SEQUENCE: 45

Ile Ser Ser Arg Ser Ser Gln Ser Ile Val His Ser Asn Gly Asn Thr
1               5                   10                  15

Tyr Leu Glu Trp Tyr Leu Gln Lys Pro Ala Gln Ser Pro Lys Leu Leu
                20                  25                  30

Ile Phe Lys Val Ser Asn Arg Phe Ser Gly Val Pro Asp Arg Phe Ser
            35                  40                  45

Arg Ser Gly Ser Gly Thr Asp Phe Thr Leu Lys Ile Ser Arg Val Glu
50                  55                  60
```

Ala Glu Asp Leu Gly Ile Tyr Tyr Cys Phe Gln Gly Ser His Val Pro
65                  70                  75                  80

Trp Thr Phe

<210> SEQ ID NO 46
<211> LENGTH: 96
<212> TYPE: PRT
<213> ORGANISM: Artificial Sequence
<220> FEATURE:
<223> OTHER INFORMATION: Synthetic peptide

<400> SEQUENCE: 46

Ser His Gly Asp Gln Ala Ser Ile Ser Ser Arg Ser Ser Gln Ser Ile
1               5                   10                  15

Val His Ser Asn Gly Asn Thr Tyr Leu Glu Trp Tyr Leu Gln Lys Pro
            20                  25                  30

Ala Gln Ser Pro Lys Leu Leu Ile Phe Lys Val Ser Asn Arg Phe Ser
        35                  40                  45

Gly Val Pro Asp Arg Phe Ser Arg Ser Gly Ser Gly Thr Asp Phe Thr
    50                  55                  60

Leu Lys Ile Ser Arg Val Glu Ala Glu Asp Leu Gly Ile Tyr Tyr Cys
65                  70                  75                  80

Ser Gln Gly Ser His Val Pro Trp Thr Phe Gly Gly Thr Lys Leu
                85                  90                  95

<210> SEQ ID NO 47
<211> LENGTH: 79
<212> TYPE: PRT
<213> ORGANISM: Artificial Sequence
<220> FEATURE:
<223> OTHER INFORMATION: Synthetic peptide

<400> SEQUENCE: 47

Ile Ser Ser Arg Ser Ser Gln Ser Ala Val His Ser Asn Gly Asn Thr
1               5                   10                  15

Tyr Leu Glu Trp Tyr Arg Arg Asn Pro Ala Gln Ser Pro Lys Leu Leu
            20                  25                  30

Ile Ile Lys Val Ser Asn Arg Phe Ser Gly Val Pro Asp Arg Phe Ser
        35                  40                  45

His Ser Gly Ser Gly Thr Asp Phe Thr Leu Lys Ile Ser Arg Val Glu
    50                  55                  60

Ala Glu Asp Leu Gly Ile Tyr Tyr Cys Phe Gln Gly Ser His Val
65                  70                  75

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Tyr Thr Phe Thr Ser Tyr Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 49

Ile Asn Pro Ser Asp Gly Asp Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Thr Arg Ser Arg Gly Gly Phe Ala Tyr
1               5

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide

<400> SEQUENCE: 51

Gln Ser Ile Val His Ser Gly Asn Thr Tyr Leu
1               5                   10

<210> SEQ ID NO 52

<400> SEQUENCE: 52

000

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Phe Gln Gly Ser His Val Pro
1               5

<210> SEQ ID NO 54
<211> LENGTH: 463
<212> TYPE: PRT
<213> ORGANISM: Artificial Sequence
<220> FEATURE:
<223> OTHER INFORMATION: Mouse antibody

<400> SEQUENCE: 54

Met Glu Trp Ile Trp Ile Phe Leu Phe Ile Leu Ser Gly Thr Ala Gly
1               5                   10                  15

Val His Ser Gln Val Gln Leu Gln Gln Ser Gly Ala Glu Leu Ala Arg
            20                  25                  30

Pro Gly Ala Ser Val Arg Leu Ser Cys Lys Ala Ser Gly Tyr Thr Phe
        35                  40                  45

Thr Gly Tyr Gly Val Ser Trp Val Lys Gln Arg Thr Gly Gln Gly Leu
    50                  55                  60

Glu Trp Val Gly Glu Ile Tyr Pro Gly Ser Gly Asn Thr Tyr Tyr Ser
65                  70                  75                  80

Glu Lys Phe Lys Gly Lys Ala Thr Leu Thr Thr Asp Lys Ser Ser Ser
                85                  90                  95
```

```
Thr Ala Tyr Met His Leu Ser Ser Leu Thr Ser Glu Asp Ser Ala Val
                100                 105                 110
Tyr Phe Cys Ala Arg Ser Ser Tyr Tyr Ser Tyr Asp Leu Phe Ala Tyr
            115                 120                 125
Trp Gly Gln Gly Thr Leu Val Thr Val Ser Ala Ala Lys Thr Thr Pro
        130                 135                 140
Pro Ser Val Tyr Pro Leu Ala Pro Gly Ser Ala Ala Gln Thr Asn Ser
145                 150                 155                 160
Met Val Thr Leu Gly Cys Leu Val Lys Gly Tyr Phe Pro Glu Pro Val
                165                 170                 175
Thr Val Thr Trp Asn Ser Gly Ser Leu Ser Ser Gly Val His Thr Phe
            180                 185                 190
Pro Ala Val Leu Gln Ser Asp Leu Tyr Thr Leu Ser Ser Ser Val Thr
        195                 200                 205
Val Pro Ser Ser Thr Trp Pro Ser Glu Thr Val Thr Cys Asn Val Ala
210                 215                 220
His Pro Ala Ser Ser Thr Lys Val Asp Lys Lys Ile Val Pro Arg Asp
225                 230                 235                 240
Cys Gly Cys Lys Pro Cys Ile Cys Thr Val Pro Glu Val Ser Ser Val
                245                 250                 255
Phe Ile Phe Pro Pro Lys Pro Lys Asp Val Leu Thr Ile Thr Leu Thr
            260                 265                 270
Pro Lys Val Thr Cys Val Val Val Asp Ile Ser Lys Asp Asp Pro Glu
        275                 280                 285
Val Gln Phe Ser Trp Phe Val Asp Asp Val Glu Val His Thr Ala Gln
290                 295                 300
Thr Gln Pro Arg Glu Glu Gln Phe Asn Ser Thr Phe Arg Ser Val Ser
305                 310                 315                 320
Glu Leu Pro Ile Met His Gln Asp Trp Leu Asn Gly Lys Glu Phe Lys
                325                 330                 335
Cys Arg Val Asn Ser Ala Ala Phe Pro Ala Pro Ile Glu Lys Thr Ile
            340                 345                 350
Ser Lys Thr Lys Gly Arg Pro Lys Ala Pro Gln Val Tyr Thr Ile Pro
        355                 360                 365
Pro Pro Lys Glu Gln Met Ala Lys Asp Lys Val Ser Leu Thr Cys Met
370                 375                 380
Ile Thr Asp Phe Phe Pro Glu Asp Ile Thr Val Glu Trp Gln Trp Asn
385                 390                 395                 400
Gly Gln Pro Ala Glu Asn Tyr Lys Asn Thr Gln Pro Ile Met Asp Thr
                405                 410                 415
Asp Gly Ser Tyr Phe Ile Tyr Ser Lys Leu Asn Val Gln Lys Ser Asn
            420                 425                 430
Trp Glu Ala Gly Asn Thr Phe Thr Cys Ser Val Leu His Glu Gly Leu
        435                 440                 445
His Asn His His Thr Glu Lys Ser Leu Ser His Ser Pro Gly Lys
450                 455                 460

<210> SEQ ID NO 55
<211> LENGTH: 294
<212> TYPE: DNA
<213> ORGANISM: Artificial Sequence
<220> FEATURE:
<223> OTHER INFORMATION: Mouse antibody

<400> SEQUENCE: 55
```

```
caggtccaac tgcagcagcc tggggctgaa ctggtgaagc ctggggcttc agtgaagctg    60
tcctgcaagg cttctggcta caccttcacc agctactgga tgcactgggt gaagcagagg   120
cctggacaag gccttgagtg gattggagag attaatccta gcaacggtcg tactaactac   180
aatgagaagt tcaagagcaa ggccacactg actgtagaca atcctccag cacagcctac    240 atgcaactca gcagcccgac atctgaggac tctgcggtct attactgtgc aaga         294
```

```
<210> SEQ ID NO 56
<211> LENGTH: 24
<212> TYPE: DNA
<213> ORGANISM: Artificial Sequence
<220> FEATURE:
<223> OTHER INFORMATION: Synthetic peptide

<400> SEQUENCE: 56
ggctacacct tcaccagtta ctat                                          24

<210> SEQ ID NO 57
<211> LENGTH: 24
<212> TYPE: DNA
<213> ORGANISM: Artificial Sequence
<220> FEATURE:
<223> OTHER INFORMATION: Synthetic peptide

<400> SEQUENCE: 57
attaatccta gcgatggtga tact                                          24

<210> SEQ ID NO 58
<211> LENGTH: 27
<212> TYPE: DNA
<213> ORGANISM: Artificial Sequence
<220> FEATURE:
<223> OTHER INFORMATION: Synthetic peptide

<400> SEQUENCE: 58
acaagatcac gtgggggttt tgcttac                                       27

<210> SEQ ID NO 59
<211> LENGTH: 33
<212> TYPE: DNA
<213> ORGANISM: Artificial Sequence
<220> FEATURE:
<223> OTHER INFORMATION: Synthetic peptide

<400> SEQUENCE: 59
cagagccttg tacacagtaa tggaaacacc tat                                33

<210> SEQ ID NO 60

<400> SEQUENCE: 60

000

<210> SEQ ID NO 61
<211> LENGTH: 21
<212> TYPE: DNA
<213> ORGANISM: Artificial Sequence
<220> FEATURE:
<223> OTHER INFORMATION: Synthetic peptide

<400> SEQUENCE: 61
tctcaaagta cacatgttcc t                                             21

<210> SEQ ID NO 62
```

```
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Gly Gly Gly Ser
1

<210> SEQ ID NO 63
<211> LENGTH: 166
<212> TYPE: PRT
<213> ORGANISM: Artificial Sequence
<220> FEATURE:
<223> OTHER INFORMATION: Synthetic peptide

<400> SEQUENCE: 63

Glu Val Gln Leu Gln Glu Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Ile
        35                  40                  45

Gly Asp Ile Asn Pro Ser Asp Gly Asp Thr Asp Phe Asn Glu Lys Phe
    50                  55                  60

Lys Ser Lys Ala Thr Leu Thr Val Asp Lys Ser Ser Ser Thr Ala Tyr
65                  70                  75                  80

Met Glu Thr Gln Leu Ser Ser Leu Thr Ser Glu Asp Ser Ala Val Tyr
                85                  90                  95

Tyr Cys Thr Arg Ser Arg Gly Gly Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Glu Thr Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu
                165

<210> SEQ ID NO 64
<211> LENGTH: 127
<212> TYPE: PRT
<213> ORGANISM: Artificial Sequence
<220> FEATURE:
<223> OTHER INFORMATION: Synthetic peptide

<400> SEQUENCE: 64

Glu Val Gln Leu Gln Val Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Ile
        35                  40                  45

Gly Asp Ile Asn Pro Ser Asp Gly Asp Thr Asp Phe Asn Glu Lys Phe
    50                  55                  60

Lys Ser Lys Ala Thr Leu Thr Val Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                 85                  90                  95

Thr Arg Ser Arg Gly Gly Phe Ala Tyr Trp Gly Gln Gly Thr Leu Val
            100                 105                 110

Thr Val Ser Ala Ala Lys Thr Thr Pro Pro Ser Val Tyr Pro Leu
        115                 120                 125

<210> SEQ ID NO 65
<211> LENGTH: 381
<212> TYPE: DNA
<213> ORGANISM: Artificial Sequence
<220> FEATURE:
<223> OTHER INFORMATION: Synthetic peptide

<400> SEQUENCE: 65
gaagttcaac tgcaggtttc tggagccgaa ctagtaaagc cgggcgcctc ggtacgctta      60
agctgcaagg catctgggta cacattcacc tcttattaca tttattgggt taaacaacgg     120
ccagggcaag gactggaatg gatcggtgat atcaatccgt ccgacggtga tacggacttt     180
aatgagaaat tcaagagtaa agctactctt acagtagata agtcctcttc cactgcctat     240
atgcaacttt cttccttgac ttcagaagac tcagccgtat actattgcac acgaagtaga     300
gggggctttg cttattgggg tcaaggaaca ctggtaacag tcagtgcggc aaagaccaca     360
ccaccgagcg tctaccctct g                                                381

<210> SEQ ID NO 66
<211> LENGTH: 100
<212> TYPE: PRT
<213> ORGANISM: Artificial Sequence
<220> FEATURE:
<223> OTHER INFORMATION: Synthetic peptide

<400> SEQUENCE: 66

Asp Val Val Met Thr Gln Thr Pro Leu Ser Leu Pro Val Ser Leu Gly
1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro
            100

<210> SEQ ID NO 67
<211> LENGTH: 300
<212> TYPE: DNA
<213> ORGANISM: Artificial Sequence
<220> FEATURE:
<223> OTHER INFORMATION: Synthetic peptide

<400> SEQUENCE: 67
gatgtggtaa tgacgcaaac accactgtcc ctaccagtaa gtttaggcga tcaagcctcc      60
atttcgtgtc gttcgtcaca aagcctggtt cactctaacg gtaatacgta tctgcattgg     120
tatttacaaa agccgggtca atccccaaaa ctcctaattt acaaggtatc aaatagattt     180
```

```
tcaggtgtcc ccgatcggtt tagcggctcg ggctcaggaa ccgatttcac acttaagatt    240
agtcgcgtgg aggctgagga cctcggtgtc tacttctgct cacagtctac gcacgtgccc    300
```